(12) United States Patent
Longo et al.

(10) Patent No.: US 12,678,305 B2
(45) Date of Patent: ***Jul. 14, 2026

(54) HYBRID STENT

(71) Applicant: Vesper Medical, Inc., Wayne, PA (US)

(72) Inventors: Michael A. Longo, Glenmoore, PA (US); William James Harrison, Signal Mountain, TN (US)

(73) Assignee: VESPER MEDICAL, INC., Wayne, PA (US)

( * ) Notice: Subject to any disclaimer, the term of this patent is extended or adjusted under 35 U.S.C. 154(b) by 916 days.

This patent is subject to a terminal disclaimer.

(21) Appl. No.: 17/836,252

(22) Filed: Jun. 9, 2022

(65) Prior Publication Data

US 2022/0296397 A1 Sep. 22, 2022

Related U.S. Application Data

(63) Continuation of application No. 16/288,744, filed on Feb. 28, 2019, now Pat. No. 11,357,650.

(51) Int. Cl.
| | |
|---|---|
| *A61F 2/915* | (2013.01) |
| *A61F 2/91* | (2013.01) |
| A61F 2/82 | (2013.01) |

(52) U.S. Cl.
CPC .......... *A61F 2/91* (2013.01); *A61F 2002/823* (2013.01); *A61F 2002/828* (2013.01); *A61F 2002/91525* (2013.01); *A61F 2002/91558* (2013.01); *A61F 2002/91575* (2013.01); *A61F 2250/0018* (2013.01)

(58) Field of Classification Search
CPC .............. A61F 2002/91558; A61F 2250/0018
See application file for complete search history.

(56) References Cited

U.S. PATENT DOCUMENTS

| | | |
|---|---|---|
| 5,064,435 A | 11/1991 | Porter |
| 5,449,373 A | 9/1995 | Pinchasik et al. |

(Continued)

FOREIGN PATENT DOCUMENTS

| | | |
|---|---|---|
| CN | 104042376 | 9/2014 |
| CN | 107773333 | 3/2018 |

(Continued)

OTHER PUBLICATIONS

Self-expanding nitinol stents of high versus low chronic outward force in de novo femoropopliteal occlusive arterial lesions (BIOFLEX-COF trial): study protocol for a randomized controlled trial (Year: 2017).*

(Continued)

*Primary Examiner* — Brian E Pellegrino

(57) ABSTRACT

A stent includes a high radial/crush force segment and a highly flexible segment. In an aspect, a plurality of first ring struts connected such that each of the plurality of first rings comprises a sinusoidal pattern having a plurality of apices and troughs, each first ring connected to an adjacent first ring by at least one connector. The connector extends from a ring strut of the first ring from a position near an apex of the first ring to a ring strut of the adjacent first rings near an apex of the adjacent ring, and a second stent segment comprises a plurality of second rings connected to one another to form a series of second rings.

30 Claims, 19 Drawing Sheets

(56) References Cited

U.S. PATENT DOCUMENTS

| | | | |
|---|---|---|---|
| 5,827,321 A | 10/1998 | Roubin et al. |
| 5,836,966 A | 11/1998 | St. Germain |
| 5,843,120 A | 12/1998 | Israel et al. |
| 5,843,175 A | 12/1998 | Frantzen |
| 5,868,780 A | 2/1999 | Lashinski et al. |
| 5,868,782 A | 2/1999 | Frantzen |
| 5,911,754 A | 6/1999 | Kanesaka et al. |
| 5,922,005 A | 7/1999 | Richter et al. |
| 5,938,697 A | 8/1999 | Killion et al. |
| 5,964,798 A | 10/1999 | Imran |
| 5,972,018 A | 10/1999 | Israel et al. |
| 6,027,526 A | 2/2000 | Limon et al. |
| 6,033,433 A | 3/2000 | Ehr et al. |
| 6,042,606 A | 3/2000 | Frantzen |
| 6,059,811 A | 5/2000 | Pinchasik et al. |
| 6,068,656 A | 5/2000 | Von Oepen |
| 6,083,259 A | 7/2000 | Frantzen |
| 6,106,548 A | 8/2000 | Roubin et al. |
| 6,113,627 A | 9/2000 | Jang |
| 6,123,721 A | 9/2000 | Jang |
| 6,146,403 A | 11/2000 | St. Germain |
| 6,156,052 A | 12/2000 | Richter et al. |
| 6,179,868 B1 | 1/2001 | Burpee et al. |
| 6,183,507 B1 | 2/2001 | Lashinski et al. |
| 6,190,403 B1 | 2/2001 | Fischell et al. |
| 6,200,334 B1 | 3/2001 | Jang |
| 6,203,569 B1 | 3/2001 | Wijay |
| 6,235,053 B1 | 5/2001 | Jang |
| 6,241,762 B1 | 6/2001 | Shanley |
| 6,261,319 B1 | 7/2001 | Kveen |
| 6,287,336 B1 | 9/2001 | Globerman et al. |
| 6,299,635 B1 | 10/2001 | Frantzen |
| 6,309,414 B1 | 10/2001 | Rolando et al. |
| 6,325,821 B1 | 12/2001 | Gaschino et al. |
| 6,325,825 B1 | 12/2001 | Kula et al. |
| 6,402,777 B1 | 6/2002 | Globerman et al. |
| 6,423,084 B1 | 7/2002 | St. Germain |
| 6,428,570 B1 | 8/2002 | Globerman et al. |
| 6,443,982 B1 | 9/2002 | Israel et al. |
| 6,451,049 B2 | 9/2002 | Vallana et al. |
| 6,461,380 B1 | 10/2002 | Cox |
| 6,461,381 B2 | 10/2002 | Israel et al. |
| 6,464,722 B2 | 10/2002 | Israel et al. |
| 6,475,236 B1 | 11/2002 | Roubin |
| 6,478,816 B2 | 11/2002 | Kveen et al. |
| 6,485,508 B1 | 11/2002 | McGuinness |
| 6,485,509 B2 | 11/2002 | Killion et al. |
| 6,497,723 B1 | 12/2002 | Starck et al. |
| 6,540,775 B1 | 4/2003 | Fischell et al. |
| 6,635,084 B2 | 10/2003 | Israel et al. |
| 6,638,300 B1 | 10/2003 | Frantzen |
| 6,641,609 B2 | 11/2003 | Globerman |
| 6,660,019 B1 | 12/2003 | Richter et al. |
| 6,679,911 B2 | 1/2004 | Burgermeister |
| 6,682,554 B2 | 1/2004 | Von Oepen et al. |
| 6,692,522 B1 | 2/2004 | Richter |
| 6,699,281 B2 | 3/2004 | Vallana et al. |
| 6,706,061 B1 | 3/2004 | Fischell et al. |
| 6,709,453 B2 | 3/2004 | Pinchasik et al. |
| 6,730,116 B1 | 5/2004 | Wolinsky et al. |
| 6,746,479 B2 | 6/2004 | Ehr et al. |
| 6,761,731 B2 | 7/2004 | Majercak |
| 6,764,506 B2 | 7/2004 | Roubin et al. |
| 6,786,922 B2 | 9/2004 | Schaeffer |
| 6,790,227 B2 | 9/2004 | Burgermeister |
| 6,818,015 B2 | 11/2004 | Hankh et al. |
| 6,923,829 B2 | 8/2005 | Boyle et al. |
| 6,939,373 B2 | 9/2005 | Gomez et al. |
| 6,945,993 B2 | 9/2005 | Kveen et al. |
| 7,004,968 B2 | 2/2006 | Lootz et al. |
| 7,029,493 B2 | 4/2006 | Majercak et al. |
| 7,037,330 B1 | 5/2006 | Rivelli, Jr. et al. |
| 7,060,088 B1 | 6/2006 | Fischell et al. |
| 7,060,090 B2 | 6/2006 | Thornton |
| 7,070,614 B1 | 7/2006 | Neuss et al. |

| | | | |
|---|---|---|---|
| 7,131,993 B2 | 11/2006 | Gregorich |
| 7,141,062 B1 | 11/2006 | Pinchasik et al. |
| 7,273,494 B2 | 9/2007 | Rolando et al. |
| 7,316,710 B1 | 1/2008 | Cheng et al. |
| 7,326,243 B2 | 2/2008 | Kveen et al. |
| 7,344,563 B2 | 3/2008 | Vallana et al. |
| 7,357,813 B2 | 4/2008 | Burgermeister |
| 7,402,169 B2 | 7/2008 | Killion |
| 7,485,130 B2 | 2/2009 | St. Germain |
| 7,527,644 B2 | 5/2009 | Mangiardi et al. |
| 7,621,947 B2 | 11/2009 | Richter et al. |
| 7,648,526 B2 | 1/2010 | Sano et al. |
| 7,686,843 B2 | 3/2010 | Moore |
| 7,731,746 B2 | 6/2010 | Kveen et al. |
| 7,806,918 B2 | 10/2010 | Nissl et al. |
| 7,862,607 B2 | 1/2011 | McDermott et al. |
| 7,896,912 B2 | 3/2011 | Shanley |
| 8,012,196 B2 | 9/2011 | Smith et al. |
| 8,016,874 B2 | 9/2011 | Casey |
| 8,034,098 B1 | 10/2011 | Callas et al. |
| 8,128,679 B2 | 3/2012 | Casey |
| 8,137,396 B2 | 3/2012 | Busold et al. |
| 8,206,427 B1 | 6/2012 | Ryan et al. |
| 8,211,163 B2 | 7/2012 | Dakin et al. |
| 8,221,489 B2 | 7/2012 | Issenmann et al. |
| 8,257,424 B2 | 9/2012 | Orlowski |
| 8,267,991 B2 | 9/2012 | Scheerder et al. |
| 8,317,854 B1 | 11/2012 | Ryan et al. |
| 8,317,859 B2 | 11/2012 | Snow et al. |
| 8,337,544 B2 | 12/2012 | Osman et al. |
| 8,348,990 B2 | 1/2013 | Boyle et al. |
| 8,470,021 B2 | 6/2013 | Magnuson |
| 8,524,132 B2 | 9/2013 | Oepen et al. |
| 8,562,665 B2 | 10/2013 | Jang |
| 8,647,379 B2 | 2/2014 | McDermott et al. |
| 8,652,196 B2 | 2/2014 | Nissl |
| 8,668,731 B2 | 3/2014 | Kveen et al. |
| 8,888,837 B2 | 11/2014 | Obradovic et al. |
| 8,974,514 B2 | 3/2015 | Anukhin |
| 9,066,825 B2 | 6/2015 | Chanduszko |
| 9,320,627 B2 | 4/2016 | Casey |
| 9,375,810 B2 | 6/2016 | Mangiardi |
| 9,408,727 B2 | 8/2016 | Ainsworth et al. |
| 9,498,360 B2 | 11/2016 | Layman et al. |
| 9,554,927 B2 | 1/2017 | Bales et al. |
| 9,561,123 B2 | 2/2017 | Bales, Jr. et al. |
| 9,622,850 B2 | 4/2017 | Bebb |
| 9,649,211 B2 | 5/2017 | Bonsignore et al. |
| 9,655,998 B2 | 5/2017 | Gemborys |
| 9,668,895 B2 | 6/2017 | Dreher |
| 9,668,898 B2 | 6/2017 | Wong |
| 9,693,860 B2 | 7/2017 | Sandstrom et al. |
| 9,700,448 B2 | 7/2017 | Snow et al. |
| 9,707,110 B2 | 7/2017 | McDermott et al. |
| 9,724,220 B2 | 8/2017 | Rasmussen |
| 9,770,348 B2 | 9/2017 | Wack |
| 9,795,496 B2 | 10/2017 | Armstrong et al. |
| 9,839,538 B2 | 12/2017 | Grewe et al. |
| 9,839,540 B2 | 12/2017 | Armstrong et al. |
| 10,271,977 B2 | 4/2019 | Longo et al. |
| 10,512,556 B2 | 12/2019 | Longo et al. |
| 10,588,764 B2 | 3/2020 | Longo et al. |
| 11,357,650 B2 * | 6/2022 | Longo ..................... A61F 2/915 623/1.15 |
| 11,628,076 B2 * | 4/2023 | Longo ..................... A61F 2/915 623/1.2 |
| 2001/0004705 A1 | 6/2001 | Killion et al. |
| 2001/0014822 A1 | 8/2001 | Milo |
| 2001/0047200 A1 | 11/2001 | White et al. |
| 2002/0013616 A1 | 1/2002 | Carter et al. |
| 2002/0042648 A1 | 4/2002 | Schaldach et al. |
| 2002/0052645 A1 | 5/2002 | Kugler |
| 2002/0058990 A1 | 5/2002 | Jang |
| 2002/0099406 A1 | 7/2002 | St Germain |
| 2003/0009214 A1 | 1/2003 | Shanley |
| 2003/0014102 A1 | 1/2003 | Hong et al. |
| 2003/0074056 A1 | 4/2003 | Killion et al. |
| 2003/0100941 A1 | 5/2003 | Fischell et al. |
| 2003/0105513 A1 | 6/2003 | Moriuchi et al. |

(56) References Cited

U.S. PATENT DOCUMENTS

| | | |
|---|---|---|
| 2003/0105517 A1 | 6/2003 | White et al. |
| 2003/0135265 A1 | 7/2003 | Stinson |
| 2003/0144724 A1 | 7/2003 | Murray, III |
| 2004/0054398 A1 | 3/2004 | Cully et al. |
| 2004/0054400 A1 | 3/2004 | Granada |
| 2004/0102835 A1 | 5/2004 | Israel et al. |
| 2004/0102838 A1 | 5/2004 | Killion |
| 2004/0133265 A1 | 7/2004 | Duffy |
| 2004/0243216 A1 | 12/2004 | Gregorich |
| 2004/0254627 A1 | 12/2004 | Thompson et al. |
| 2004/0267350 A1 | 12/2004 | Roubin et al. |
| 2005/0004657 A1 | 1/2005 | Burgermeister |
| 2005/0021130 A1 | 1/2005 | Kveen |
| 2005/0060024 A1 | 3/2005 | Lee et al. |
| 2005/0080479 A1 | 4/2005 | Feng et al. |
| 2006/0025852 A1 | 2/2006 | Armstrong et al. |
| 2006/0129227 A1 | 6/2006 | Hengelmolen |
| 2006/0173531 A1 | 8/2006 | Richter |
| 2007/0010869 A1 | 1/2007 | Sano |
| 2007/0213806 A1 | 9/2007 | Roubin et al. |
| 2007/0213807 A1 | 9/2007 | Roubin et al. |
| 2007/0219613 A1 | 9/2007 | Kao et al. |
| 2007/0260300 A1 | 11/2007 | Gregorich et al. |
| 2008/0009938 A1 | 1/2008 | Huang et al. |
| 2008/0046072 A1 | 2/2008 | Laborde et al. |
| 2008/0051878 A1 | 2/2008 | Cheng et al. |
| 2008/0140181 A1 | 6/2008 | Reynolds et al. |
| 2008/0262593 A1 | 10/2008 | Ryan et al. |
| 2008/0288048 A1 | 11/2008 | Rolando et al. |
| 2009/0018641 A1 | 1/2009 | Binkert |
| 2009/0062899 A1 | 3/2009 | Dang et al. |
| 2009/0099652 A1 | 4/2009 | Granada |
| 2009/0264979 A1 | 10/2009 | Kao et al. |
| 2010/0004736 A1 | 1/2010 | Rolando et al. |
| 2010/0042202 A1 | 2/2010 | Ramzipoor et al. |
| 2010/0131044 A1 | 5/2010 | Patel |
| 2010/0222864 A1 | 9/2010 | Rivelli, Jr. et al. |
| 2010/0241216 A1 | 9/2010 | Rolando et al. |
| 2010/0274346 A1 | 10/2010 | Chouinard et al. |
| 2010/0274348 A1 | 10/2010 | Schaffner et al. |
| 2011/0106237 A1 | 5/2011 | Bonsignore |
| 2011/0125251 A1 | 5/2011 | Cottone et al. |
| 2011/0230957 A1 | 9/2011 | Bonsignore et al. |
| 2011/0264186 A1 | 10/2011 | Berlung et al. |
| 2011/0301685 A1 | 12/2011 | Kao |
| 2012/0043703 A1 | 2/2012 | Von Oepen et al. |
| 2012/0046729 A1 | 2/2012 | Von Oepen et al. |
| 2012/0046730 A1 | 2/2012 | Von Oepen et al. |
| 2012/0046731 A1 | 2/2012 | Von Oepen et al. |
| 2012/0046733 A1 | 2/2012 | Von Oepen et al. |
| 2012/0046739 A1 | 2/2012 | Von Oepen et al. |
| 2012/0143312 A1 | 6/2012 | Brown |
| 2012/0277844 A1 | 11/2012 | Wu |
| 2012/0310327 A1 | 12/2012 | McHugo |
| 2013/0178928 A1 | 7/2013 | Vyas et al. |
| 2013/0289708 A1 | 10/2013 | Cox et al. |
| 2013/0304192 A1 | 11/2013 | Chanduszko |
| 2013/0325141 A1 | 12/2013 | Gill |
| 2014/0025157 A1 | 1/2014 | Abunassar |
| 2014/0277332 A1 | 9/2014 | Slazas et al. |
| 2014/0277365 A1 | 9/2014 | Gillespie |
| 2014/0277378 A1 | 9/2014 | Lane et al. |
| 2015/0105852 A1 | 4/2015 | Noffke et al. |
| 2015/0209167 A1 | 7/2015 | Mangiardi |
| 2015/0250580 A1 | 9/2015 | Besselink |
| 2015/0265437 A1 | 9/2015 | Fleury et al. |
| 2016/0113789 A1 | 4/2016 | Fleury et al. |
| 2016/0135970 A1 | 5/2016 | Schaeffer et al. |
| 2016/0235562 A1 | 8/2016 | Casey |
| 2016/0250052 A1 | 9/2016 | Kaspar |
| 2016/0287418 A1 | 10/2016 | Cheng et al. |
| 2017/0035548 A1 | 2/2017 | Bebb et al. |
| 2017/0071768 A1 | 3/2017 | Krieger et al. |
| 2017/0086994 A1 | 3/2017 | Bales et al. |
| 2017/0100267 A1 | 4/2017 | Bales et al. |
| 2017/0224878 A1 | 8/2017 | Gemborys |
| 2017/0265998 A1 | 9/2017 | Sandstrom et al. |
| 2017/0312104 A1 | 11/2017 | McDermott et al. |
| 2017/0312105 A1 | 11/2017 | McDermott et al. |
| 2017/0340464 A1 | 11/2017 | Kovach et al. |
| 2018/0055665 A1 | 3/2018 | Gorochow |
| 2018/0256378 A1 | 9/2018 | Callister |
| 2018/0318113 A1 | 11/2018 | Sirhan et al. |
| 2020/0197200 A1 | 6/2020 | Longo et al. |
| 2020/0276036 A1 | 9/2020 | Longo et al. |

FOREIGN PATENT DOCUMENTS

| | | |
|---|---|---|
| EP | 0800801 | 10/1997 |
| EP | 1059894 | 12/2000 |
| JP | 2002530146 A | 9/2002 |
| JP | 2007-500051 | 1/2007 |
| JP | 2013-528112 | 7/2013 |
| JP | 2014-138851 | 7/2014 |
| WO | 2015/038790 | 3/2015 |
| WO | 2016/046413 | 3/2016 |
| WO | 2017/042329 | 3/2017 |
| WO | 2017/050710 | 3/2017 |

OTHER PUBLICATIONS

International Search Report and Written Opinion dated Jun. 8, 2020, from International Application No. PCT/US2020/019791, 12 pages.
International Search Report and Written Opinion dated Nov. 19, 2018, from International Application No. PCT/US2018/049656, 10 pages.
International Preliminary Report on Patentability dated Mar. 19, 2020, from International Application No. PCT/US2018/049656, 9 pages.
Supplementary European Search Report dated May 10, 2021, from related Application No. EP 18854282, 9 pages.
Office Action issued in co-pending U.S. Appl. No. 15/861,465, dated Oct. 9, 2018 (now issued on Dec. 24, 2019 as U.S. Pat. No. 10,512,556).
Office Action issued in co-pending U.S. Appl. No. 15/861,465, dated Apr. 11, 2019 (now issued on Dec. 24, 2019 as U.S. Pat. No. 10,512,556).
Notice of Allowance issued in co-pending U.S. Appl. No. 15/861,465, dated Aug. 21, 2019 (now issued on Dec. 24, 2019 as U.S. Pat. No. 10,512,556).
Office Action issued for U.S. Appl. No. 16/799,233, dated Sep. 28, 2021 (now issued on Jul. 5, 2022 as U.S. Pat. No. 11,376,142).
Notice of Allowance issued for U.S. Appl. No. 16/799,233, dated Jan. 20, 2022 (now issued on Jul. 5, 2022 as U.S. Pat. No. 11,376,142).
Office Action issued for Japanese Application No. 2020-513897, dated Nov. 9, 2022 (and English Translation).
Office Action and Search Report issued for Chinese Application No. 201880058236.7, dated Oct. 8, 2022 (and English Translation).
Office Action issued for Japanese Application No. 2020-513897, dated Apr. 1, 2022.

* cited by examiner

HYBRID STENT

CROSS-REFERENCE TO RELATED APPLICATIONS

This application is a continuation application of U.S. patent application Ser. No. 16/288,744, filed Feb. 28, 2019, the disclosure of which is incorporated herein by reference in its entirety.

BACKGROUND

Field of the Invention

Disclosed herein are stents for implantation within the body and methods for delivery and/or deployment. Certain embodiments disclosed herein may be used in procedures to treat May-Thurner syndrome and/or deep venous thrombosis and the resulting post-thrombotic syndrome.

Description of the Related Art

May-Thurner syndrome, also known as iliac vein compression syndrome, is a condition in which compression of the common venous outflow tract of the left lower extremity may cause various adverse effects, including, but not limited to, discomfort, swelling, pain, and/or deep venous thrombosis (DVT) (commonly known as blood clots). May-Thurner syndrome occurs when the left common iliac vein is compressed by the overlying right common iliac artery, leading to stasis of blood, which may cause the formation of blood clots in some individuals. Other, less common, variations of May-Thurner syndrome have been described, such as compression of the right common iliac vein by the right common iliac artery.

While May-Thurner syndrome is thought to represent between two to five percent of lower-extremity venous disorders, it frequently goes unrecognized. Nevertheless, it is generally accepted that May-Thurner syndrome is about three times more common in women than it is in men and typically manifests itself between the age of twenty and forty. Patients exhibiting both hypercoagulability and left lower extremity thrombosis may be suffering from May-Thurner syndrome. To confirm that diagnosis, it may be necessary to rule out other causes for hypercoagulable state, for example by evaluating levels of antithrombin, protein C, protein S, factor V Leiden, and prothrombin G20210A.

By contrast to the right common iliac vein, which ascends almost vertically parallel to the inferior vena cava, the left common iliac vein takes a more transverse course. Along this course, it lies under the right common iliac artery, which may compress it against the lumbar spine. Iliac vein compression is a frequent anatomic variant—it is thought that as much as 50% luminal compression of the left iliac vein occurs in a quarter of healthy individuals. However, compression of the left common iliac vein becomes clinically significant only if such compression causes appreciable hemodynamic changes in venous flow or venous pressure, or if it leads to acute or chronic deep venous thrombosis, which will be discussed in more detail below. In addition to the other problems associated with compression, the vein may also develop intraluminal fibrous spurs from the effects of the chronic pulsatile compressive force from the overlying artery.

The narrowed, turbulent channel associated with May-Thurner syndrome may predispose the afflicted patient to thrombosis. And, the compromised blood flow often causes collateral blood vessels to form—most often horizontal transpelvis collaterals, connecting both internal iliac veins to create additional outflow possibilities through the right common iliac vein. Sometimes vertical collaterals are formed, most often paralumbar, which can cause neurological symptoms, like tingling and numbness.

Current best practices for the treatment and/or management of May-Thurner syndrome is proportional to the severity of the clinical presentation. Leg swelling and pain is best evaluated by vascular specialists, such as vascular surgeons, interventional cardiologists, and interventional radiologists, who both diagnose and treat arterial and venous diseases to ensure that the cause of the extremity pain is evaluated. Diagnosis of May-Thurner syndrome is generally confirmed one or more imaging modalities that may include magnetic resonance venography, and venogram, which, because the collapsed/flattened left common iliac may not be visible or noticed using conventional venography, are usually confirmed with intravascular ultrasound. To prevent prolonged swelling or pain as downstream consequences of the left common iliac hemostasis, blood flow out of the leg should be improved/increased. Early-stage or uncomplicated cases may be managed simply with compression stockings. Late-stage or severe May-Thurner syndrome may require thrombolysis if there is a recent onset of thrombosis, followed by angioplasty and stenting of the iliac vein after confirming the diagnosis with a venogram or an intravascular ultrasound. A stent may be used to support the area from further compression following angioplasty. However, currently available stenting options suffer from several complications—including severe foreshortening, lack of flexibility (which can force the vessel to straighten excessively), vessel wear and eventual performation, increased load on and deformation of the stent causing early fatigue failure, and/or impedence of flow in the overlying left iliac artery potentially causing peripheral arterial disease. The compressed, narrowed outflow channel present in May-Thurner syndrome may cause stasis of the blood, which an important contributing factor to deep vein thrombosis.

Some patients suffering from May-Thurner syndrome may exhibit thrombosis while others may not. Nevertheless, those patients that do not experience thrombotic symptoms may still experience thrombosis at any time. If a patient has extensive thrombosis, pharmacologic and/or mechanical (i.e., pharmacomechanical) thrombectomy may be necessary. The hemostasis caused by May-Thurner syndrome has been positively linked to an increased incidence of deep vein thrombosis ("DVT").

Deep vein thrombosis, or deep venous thrombosis, is the formation of a blood clot (thrombus) within a deep vein, predominantly in the legs. The right and left common iliac are common locations for deep vein thrombosis, but other locations of occurrence are common. Non-specific symptoms associated with the condition may include pain, swelling, redness, warmness, and engorged superficial veins. Pulmonary embolism, a potentially life-threatening complication of deep vein thrombosis, is caused by the detachment of a partial or complete thrombus that travels to the lungs. Post-thrombotic syndrome, another long-term complication associated with deep venous thrombosis, is a medical condition caused by a reduction in the return of venous blood to the heart and can include the symptoms of chronic leg pain, swelling, redness, and ulcers or sores.

Deep vein thrombosis formation typically begins inside the valves of the calf veins, where the blood is relatively oxygen deprived, which activates certain biochemical pathways. Several medical conditions increase the risk for deep vein thrombosis, including cancer, trauma, and antiphospholipid syndrome. Other risk factors include older age, surgery, immobilization (e.g., as experienced with bed rest, orthopedic casts, and sitting on long flights), combined oral contraceptives, pregnancy, the postnatal period, and genetic factors. Those genetic factors include deficiencies with antithrombin, protein C, and protein S, the mutation of Factor V Leiden, and the property of having a non-O blood type. The rate of new cases of deep vein thrombosis increases dramatically from childhood to old age; in adulthood, about 1 in 1000 adults develops the condition annually.

Common symptoms of deep vein thrombosis include pain or tenderness, swelling, warmth, redness or discoloration, and distention of surface veins, although about half of those with the condition have no symptoms. Signs and symptoms alone are not sufficiently sensitive or specific to make a diagnosis, but when considered in conjunction with known risk factors can help determine the likelihood of deep vein thrombosis. Deep vein thrombosis is frequently ruled out as a diagnosis after patient evaluation: the suspected symptoms are more often due to other, unrelated causes, such as cellulitis, Baker's cyst, musculoskeletal injury, or lymphedema. Other differential diagnoses include hematoma, tumors, venous or arterial aneurysms, and connective tissue disorders.

Anticoagulation, which prevents further coagulation but does not act directly on existing clots, is the standard treatment for deep vein thrombosis. Other, potentially adjunct, therapies/treatments may include compression stockings, selective movement and/or stretching, inferior vena cava filters, thrombolysis, and thrombectomy.

In any case, treatment of various venous maladies, including those described above, can be improved with stents. Improvements in stents for venous use are therefore desired.

BRIEF SUMMARY OF THE INVENTION

Accordingly, the present invention is directed to an intravascular stent that obviates one or more of the problems due to limitations and disadvantages of the related art.

In an aspect of the present invention, a stent comprises a first stent segment, the first stent segment having a first radial/crush force RF1 and a first diameter D1; and a second stent segment, the second stent segment having a second radial/crush force RF2 and a second diameter D2; wherein RF1>RF2.

In another aspect of the present invention, a stent system comprises a first stent, comprising a first stent segment, the first stent segment having a radial/crush force RF1 and a diameter D1; and a second stent segment, the second stent segment having a radial/crush force RF2 and a diameter D2; wherein RF1>RF2; an additional stent having a radial/crush force RF4, the additional stent having an end region configured to overlap a portion of the second stent segment in vivo.

Another embodiment includes a method of delivering the stent having a first segment having a first radial/crush for RF1 and a first diameter D1 and a second segment having a second radial/crush force RF2 and a second diameter D2. The method includes crimping a stent onto a catheter including radially compressing and lengthening a plurality of rings connected by flexible connectors; placing the first segment at a target location and expanding the first segment and subsequently placing the second segment and expanding the second segment wherein RF1>RF2.

Further embodiments, features, and advantages of the intravascular stent, as well as the structure and operation of the various embodiments of the intravascular stent, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS

The accompanying figures, which are incorporated herein and form part of the specification, illustrate an intravascular stent. Together with the description, the figures further serve to explain the principles of the intravascular stent described herein and thereby enable a person skilled in the pertinent art to make and use the intravascular stent.

DETAILED DESCRIPTION

Accurate placement is ideal in all medical interventions, but it is vital in areas where the end that is first deployed is critical. Such areas include at vessel bifurcations and branch vessels, so that the implant does not enter or interfere with the portion of the vessel that does not require treatment. Such a bifurcation is present at the inferior vena cava where it branches into right and left iliac veins, as described in more detail below.

Figure 1:
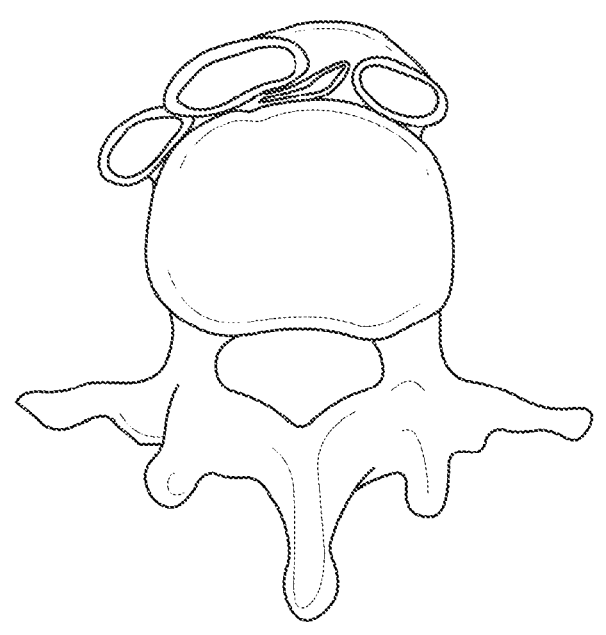
FIG. 1 shows an inferior-posterior view of the L5 lumbar and the bifurcations of the abdominal aorta and inferior vena cava.

May-Thurner syndrome, or iliac vein compression syndrome, occurs in the peripheral venous system when the iliac artery compresses the iliac vein against the spine as shown in FIG. 1. FIG. 1 illustrates a vertebra, the right and left common iliac arteries near the bifurcation of the abdominal aorta, and the right and left common iliac arteries near the bifurcation of the inferior vena cava. The bifurcations generally occur near the L5 lumbar vertebra. Thus, it can be seen that FIG. 1 shows an inferior-posterior view of the L5 lumbar and the bifurcations of the abdominal aorta and inferior vena cava.

As shown, the strong right common iliac artery has compressed the iliac vein causing it to become narrowed. This is one possible, if not a classic, manifestation of May-Thurner syndrome. Over time, such narrowing may cause vascular scarring which can result in intraluminal changes that could precipitate iliofemoral venous outflow obstruction and/or deep vein thrombosis. As discussed above, venous insufficiency (i.e., a condition in which the flow of blood through the veins is impaired) can ultimately lead to various deleterious pathologies including, but not limited to, pain, swelling, edema, skin changes, and ulcerations. Venous insufficiency is typically brought on by venous hypertension that develops as a result of persistent venous obstruction and incompetent (or subcompetent) venous valves. Current treatments for venous outflow obstruction include anticoagulation, thrombolysis, balloon angioplasty and stenting.

Figure 2:
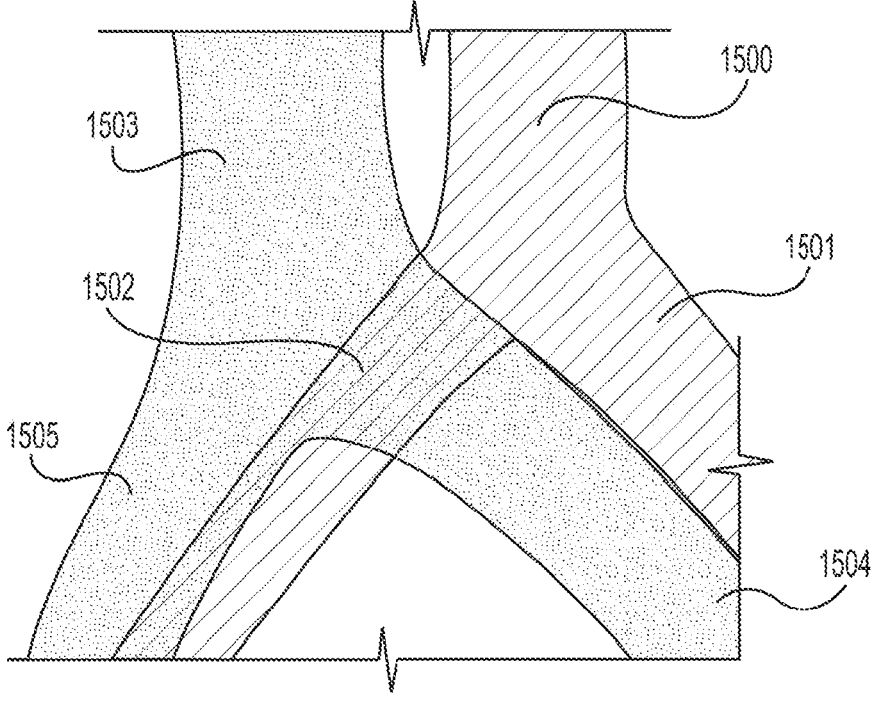
FIG. 2 shows a schematic of the standard overlap of the right common iliac artery over the left common iliac vein.

FIG. 2 illustrates the standard overlap of the right common iliac artery over the left common iliac vein. The arteries shown include the abdominal aorta 1500 branching into the left common iliac artery 1501 and the right common iliac artery 1502. The veins shown include the inferior vena cava 1503 branching into the left common iliac vein 1504 and right common iliac vein 1505. It will be understood that the rough diagram illustrated in FIG. 2 represents the view looking down on a patient laying face-up (i.e., an anterior-poster view of the patient at the location of the bifurcation of the abdominal aorta 1500 and the inferior vena cava 1503). The overlap of the right common iliac artery 1502, which is relatively strong and muscular, over the left common iliac vein 1504 can cause May-Thurner syndrome by pressing down on the vein 1504, crushing it against the spine, restricting flow, and, eventually, causing thrombosis and potentially partially or completely clotting off of the left common iliac vein 1504 and everything upstream of it (i.e., the venous system in the left leg, among others).

Figure 3:
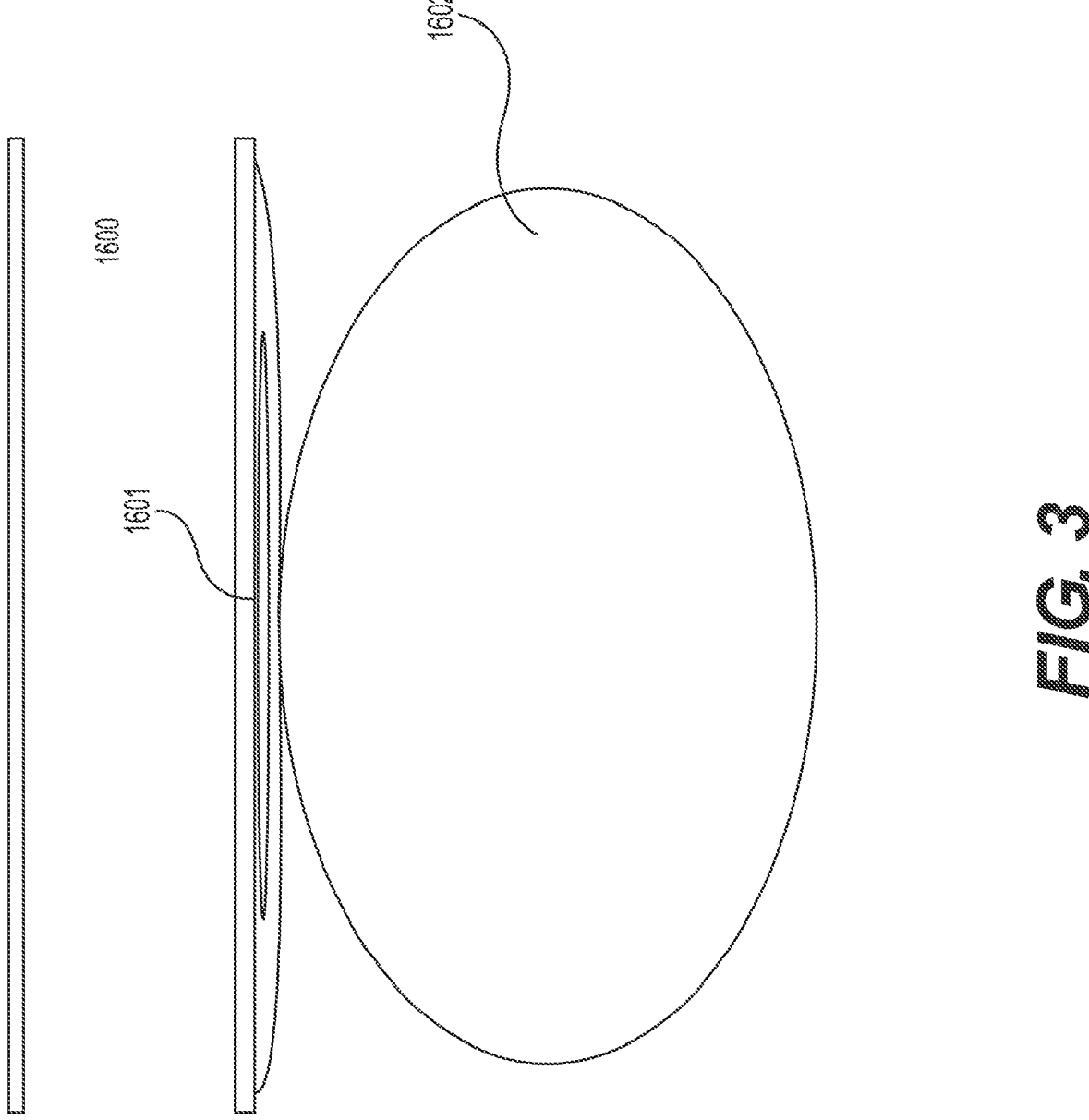
FIG. 3 shows a cross-sectional schematic of the arteriovenous system shown in FIG. 2.

FIG. 3 illustrates a cross-section of the arterio-venous system shown in FIG. 2 taken along the gray dotted line. Shown in schematic are the right common iliac artery 1600, the left common iliac vein 1601, and a vertebra 1602 of the spine (possibly the L5 lumbar vertebra of the lumbar spine). As can be seen, the right common iliac artery 1600 is substantially cylindrical, due to its strong, muscular construction (among other potential factors). That strong, muscular artery has pressed down on the left common iliac vein 1601, until it has almost completely lost patency, i.e., it is nearly completely pinched off. It will be understood that May-Thurner syndrome may indeed involve such severe pinching/crushing of the underlying left common iliac vein 1601 against the vertebra 1602 of the lumbar spine. However, it will also be understood that May-Thurner syndrome may involve much less pinching/crushing of the underlying left common iliac vein 1601 against the vertebra 1602. Indeed, embodiments disclosed herein are appropriate for the treatment of various degrees of May-Thurner syndrome, including full crushing/pinching of the left common iliac vein 1602 by the right common iliac artery 1600. Other embodiments disclosed herein are appropriate for the treatment of various degrees of May-Thurner syndrome, including, but not limited to a crush/pinch of the underlying left common iliac vein 1601 of between about 10-95%, about 15-90%, about 20-85%, about 25-80%, about 30-75%, about 35-70%, about 40-65%, about 45-60%, and about 50-55%, or any other crush/pinch that could merit treatment using one or more of the devices disclosed herein.

Generally, disclosed herein are stents that include circumferential rings of alternating interconnected struts connected by flexible connectors. The stent may have open or closed cells of various configuration formed by an expandable material. The final expanded implanted configuration can be achieved through mechanical expansion/actuation (e.g., balloon-expandable) or self-expansion (e.g., Nitinol). An exemplary embodiment of the stents described herein are self-expanding implants comprising super elastic or shape memory alloy materials, but the stent is not so limited and may be formed of balloon-expandable material. According to an aspect of the present disclosure, an expandable stent has varying magnitudes of radial force, crush resistance and flexibility at different locations along the length of the stent, while at the same time, the different locations have the same or similar diameter in an expanded configuration of the stent.

Figure 6:
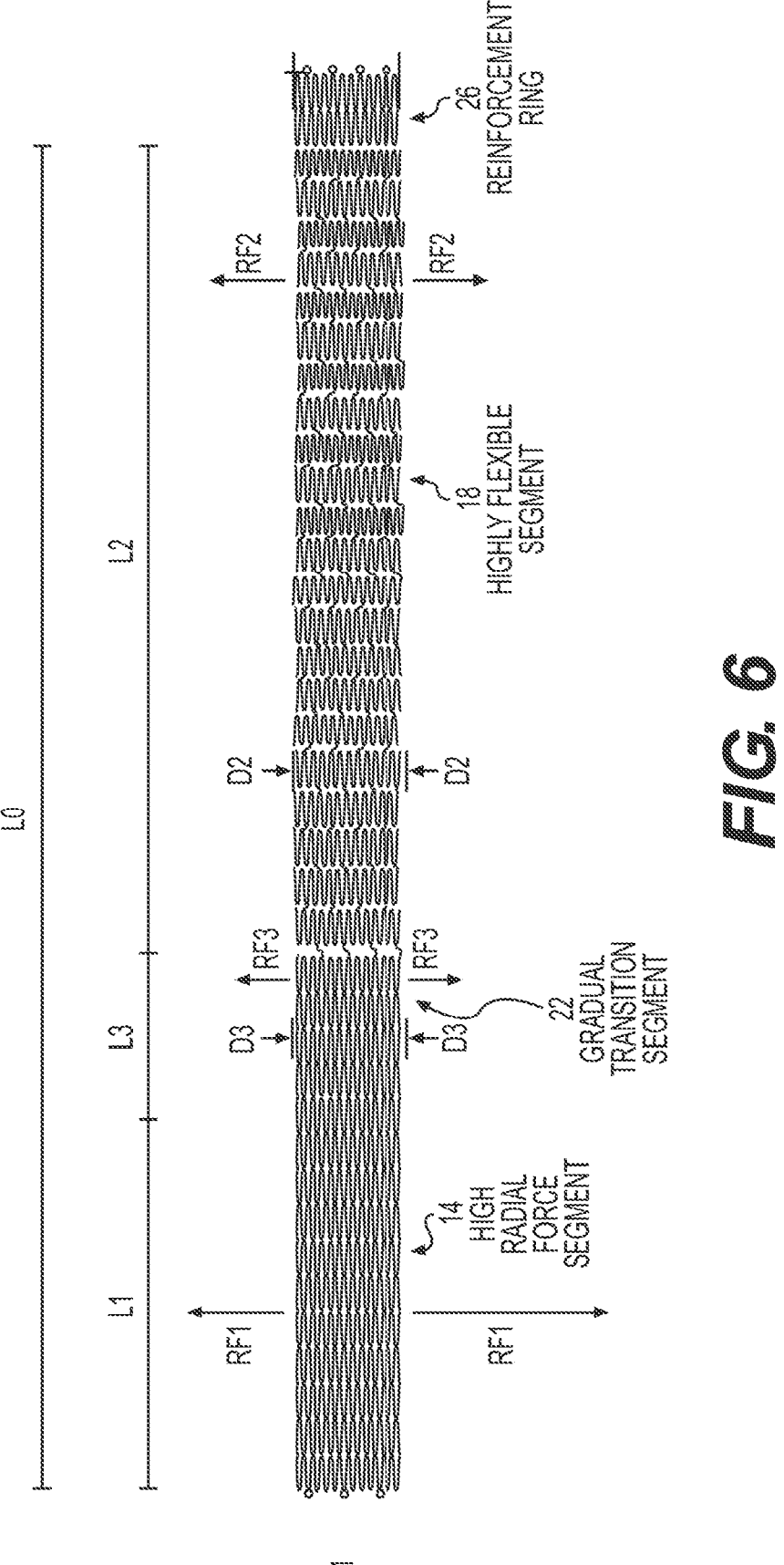
FIG. 6 illustrates an exemplary hybrid stent according to principles of the present disclosure.

As illustrated in FIG. 6, an exemplary stent 10 includes a high radial/crush force segment 14, a highly flexible segment 18 and a transition segment 22 between the high radial/crush force segment 14 and the highly flexible segment 18. The exemplary stent 10, as illustrated in FIG. 6, may include a reinforcement ring 26 at an end of the stent 10, for example, adjacent the highly flexible segment 18 (configuration shown) or adjacent the high radial/crush force segment 14 (configuration not shown). In an embodiment according to principles described herein, the stent 10 having a high radial/crush force segment 14 and a highly flexible segment 18 may be cut from a single tube, such as nitinol, for example, but could also be formed or cut from flat sheets that are welded together at long edges to form a tube-like structure. While a transition segment is illustrated herein, it should be noted that a hybrid stent that does not include a transition segment is considered to be within the scope of this disclosure.

Figure 4:
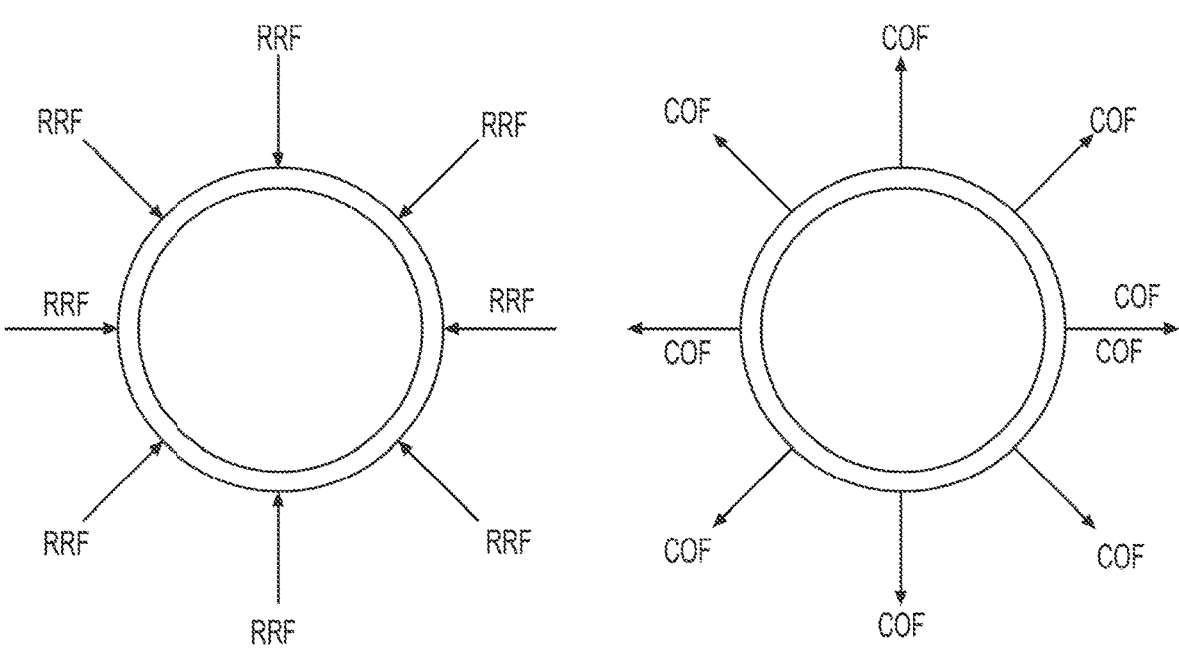
FIG. 4 illustrates radial force as radial resistive force or chronic outward force.
Figure 5:
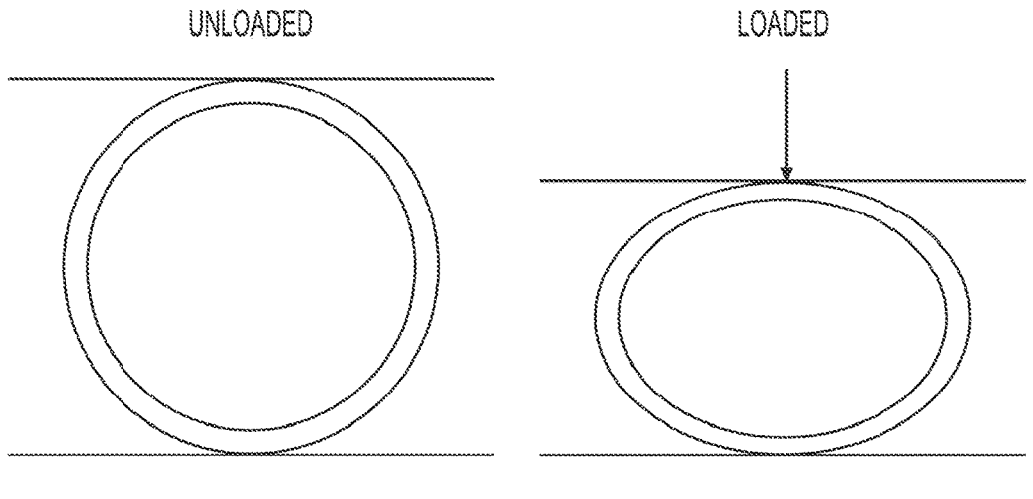
FIG. 5 illustrates crush resistance force and load on an exemplary stent.

Generally radial force refers to both or either Radial Resistive Force (RRF) and Chronic Outward Force (COF). As shown in FIG. 4, radial resistive force is an external force that acts around the circumference of a stent on the stent (toward the center of the stent). Chronic outward force is the force the sent exerts outward from a direction of the center of the stent. Chronic outward force of a stent will cause the stent to exert force on the vessel in which it is inserted to resist collapse and keep the vessel open. FIG. 5 illustrates crush resistance, as used herein. Crush resistance is a force of the stent when subject to a flat plate/focal crush load. While the radial force vector directions in FIG. 6 illustrate chronic outward force, the radial force according to principles of the present disclosure may be radial resistive force, which is more related to crush resistance than a chronic outward force. Vectors illustrated in the figures are meant to indicate direction, not magnitude. Although Radial Force and Crush Resistance can be related they do not necessarily drive each other. So a stent may be designed to have high crush resistance (flat plate/focal) but not high radial force. Such attributes can be tested independently in different test configurations.

The reinforcement ring may be an area of greater stiffness/crush resistance at an end portion of the stent. "Greater stiffness" here means having a stiffness/crush resistance greater than a portion of the stent adjacent the reinforcement ring. The reinforcement ring having greater stiffness may provide good inflow into the stent and through the vessel having the implant therein. While described herein as a "reinforcement ring," the area of greater stiffness may be provided by an additional structure overlying the stent end (e.g., a "ring") or may instead be an area where the strut structure is actually stronger, e.g. because the material forming the area of greater stiffness is inherently stiffer, a tighter cell structure, thicker struts or the like. For example, the reinforcement ring may have a different stent geometry, e.g., different strut width or is simply a fully-connected ring.

Figure 7:
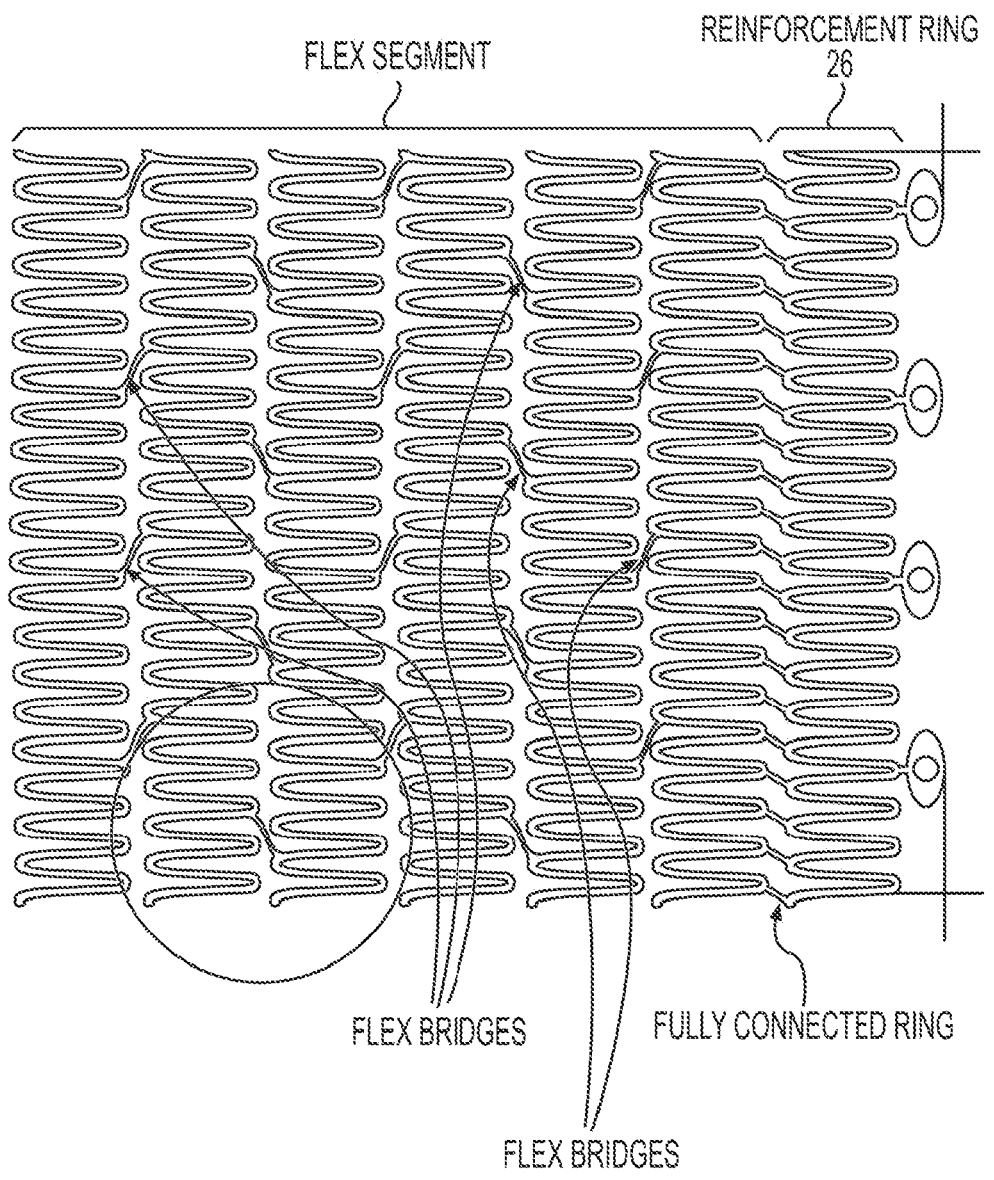
FIG. 7 illustrates an exemplary reinforcement ring according to principles of the present disclosure.

An exemplary embodiment of the reinforcement ring is illustrated in FIG. 7. As can be seen in FIG. 7, more of the ring struts making up the reinforcement ring are connected by flexible connectors/bridges to the adjacent ring than in the neighboring highly flexible segment.

Returning to the stent structure, as illustrated in FIG. 6, a length of stent 10 having length L0 includes high radial force segment 14 having a radial force and/or crush resistance RF1 and a flexibility F1 along the length L1 of the high radial/crush force segment 14. That is, a radial/crush resistive force RF1 of the high radial/crush force segment 14 is relatively greater than the remainder of the stent 10, and may be in the range of 0.75 to 1.00 N/mm, for example. The flexibility F1 of the high radial/crush force segment 14 may also be relatively lower than the remainder of the stent 10. Flexibility is evaluated/measured through angle of deflection. According to principles described herein, the high radial/crush force segment may be designed to withstand long term durability (fatigue) testing with a flexion range of 0-60 degrees.

The relatively high radial/crush force segment 14 is intended to be placed in a vessel in the region of the vessel prone to compression or crushing, such as pinching/crushing of the underlying left common iliac vein 1601 against the vertebra 1602 caused by May-Thurner syndrome, as illustrated in FIG. 3. The high radial/crush force segment has a diameter D1.

The length of stent L0 also includes a highly flexible segment 18, which has relatively greater flexibility than the high radial/crush force 14 segment along the length of the highly flexible segment 18. In addition, according principles of the present disclosure, the highly flexible segment 18 has a length L2, a diameter D2 and radial force, crush resistance RF2 and flexibility F2, where RF2<RF1 and F2>F1, such that the highly flexible segment is more flexible than the high radial/crush force segment 14. According to principles described herein, the highly flexible segment may be designed to withstand long term durability (fatigue) testing with a flexion range of 0-140 degrees. A radial resistive force RF2 of the highly flexible segment 18 may be in the range of 0.50 to 0.70 N/mm, for example.

The length of stent 10 may also include a transition segment 22 between the high radial/crush force segment 14 and the highly flexible segment 18, where the transition segment 22 has a length L3, a diameter D3 and radial force or radial resistive force (crush resistance) RF3 and flexibility F3, where RF1>RF3>RF2 and F1 and F2>F3>F1. The radial force or radial resistive force (crush resistance) RF3 and flexibility F3 of the transition segment 22 may vary over the length L3 of the transition segment 22 or may be constant along the length L3 of the transition segment 22.

Each of the high radial/crush force segment 14, transition segment 22 and highly flexible segment 18 has a different radial force, crush resistance and flexibility, which may be provided by different ring structures in each segment of the stent 10. As can be observed in FIG. 6, a high radial force segment 14 may have a cell structure that has relatively greater periodicity, may be formed of stiffer ring struts and flexible connectors, and/or may have a more closed cell structure or other structure to impart the desired radial force or crush resistance relative to the radial force or crush resistance of the highly flexible segment. For example, the strut geometry, thicker/wider struts provide more radial strength, number of apexes around the circumference of the stent/ring geometry can all drive radial force up or down, and the configuration/connection to the adjacent rings through the bridge connectors and more ring connectors can increase radial force. Similarly, the highly flexible segment 18 may have a cell structure that has relatively lesser periodicity, may be formed of relatively more flexible ring struts and flexible connectors, and/or have a more open cell structure. The transition segment may have a cell structure that transitions a geometry of the rings struts and flexible connectors of the high radial/crush force segment to a geometry of the highly flexible segment, or the transition segment may have a different cell structure than the high radial/crush force segment and the highly flexible segment. In an embodiment according to principles described herein, the stent having a high radial/crush force segment, a transition segment and a highly flexible segment may be cut from a single tube, such as nitinol, for example, but may also be formed by any other suitable means.

In the illustrated embodiment of FIG. 6, each of the segments of the stent has substantially the same diameter, such that D1≈D2≈D3. In another embodiment, the stent can be tapered such that D1>D2>D3. As described herein, one stent can treat a range of vein vessel diameters. The present stent structure may allow a single stent to treat multiple vessel sizes as the force exerted on the vessel remains fairly consistent over a range of diameters (3-4 mm). This is different than conventional stents in that most conventionally stents need to be specifically sized to the vessel they are treating (i.e., 0.5 mm-1.0 mm of oversizing). Thus, most conventional stents are offered in 2 mm increments (e.g., 10 mm, 12 mm, 14 mm, etc.). Adaptive diameter according to principles described herein simplifies sizing decisions for the doctor and allows a single stent to treat a long segment of vein, as the vein diameter generally reduces in diameter in the proximal direction.

It is contemplated that the length L2 of the highly flexible segment 18 will be greater than the length L1 of the high radial/crush force segment which will be greater than the length L3 of the transition segment.

Figure 8:
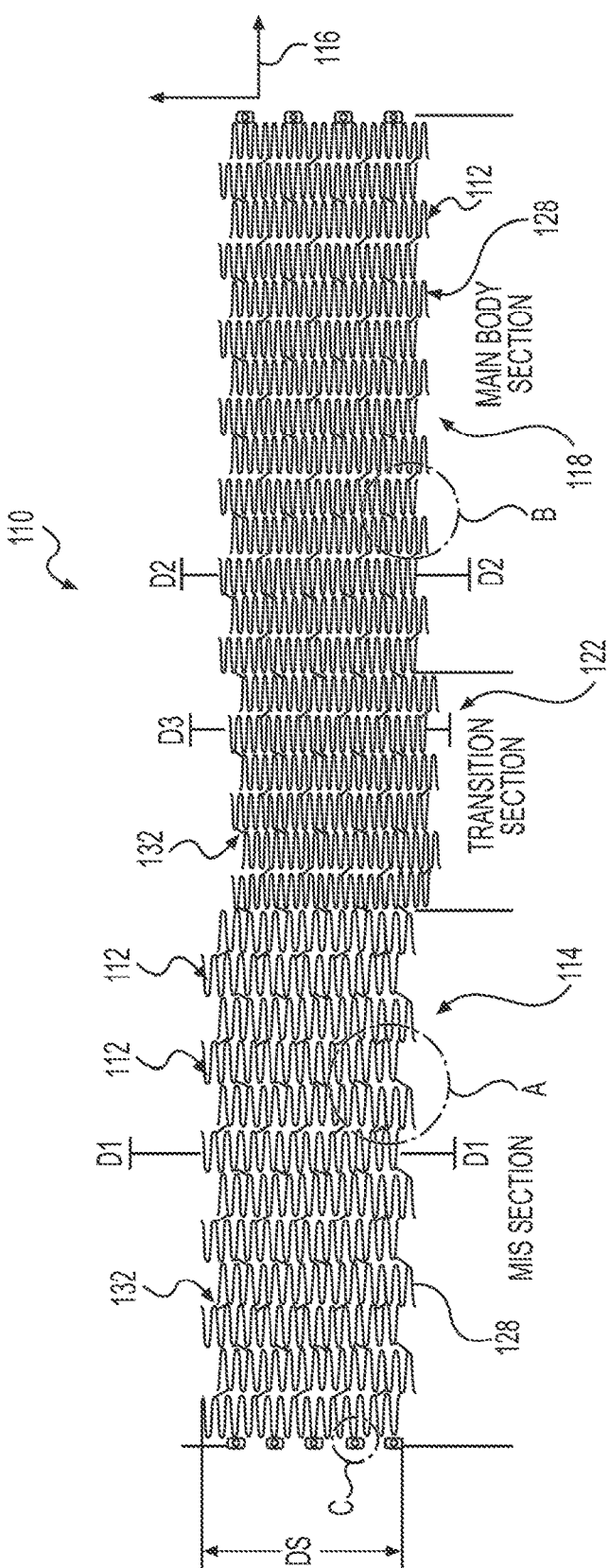
FIG. 8 illustrates an exemplary embodiment of a hybrid stent according to principles of the present disclosure.

An exemplary embodiment structure of a stent 110 according to principles of the present disclosure is shown in FIG. 8. As illustrated in FIG. 8, the diameter DS along the stent 110 at any given ring 112 is substantially the same (D1≈D2≈D3). In the embodiment illustrated in FIG. 8, each of the high radial/crush force segment (May-Thurner Syndrome "MTS" Section) 114, the transition segment (Transition Section) 122 and the highly flexible segment (Main Body Section) 118, has a similar cell pattern. In such case, the radial force or crush resistance RF of the segments may be varied by varying the thickness of the struts and/or flexible connectors 132 or the angular relationship of the struts with other struts and/or with the flexible connectors and/or the angulation of the flexible connectors themselves.

It should be noted that terms such as perpendicular, thickness, same, similar, and other dimensional and geometric terms should not be regarded as strict or perfect in their application. Instead, geometric and other dimensional reference terms should be interpreted based on their correspondence to accepted manufacturing tolerances and functional needs of the stent 110 on which they are employed. For example, the term "perpendicular" should be appreciated as affording a reasonable amount of angular variation due to manufacturing imperfections or the actual intentional curves cut or formed in the stent design 110. Also, any thickness, width or other dimension should be assessed based on tolerances and functional needs of the design rather than idealized measurements.

The thickness of the strut 128, on the other hand, is its depth in the radial direction which is generally perpendicular to the strut width measurement, as shown in FIG. 8. The strut thickness 128 normally corresponds to the wall thickness (outside diameter minus inside diameter) of the tube from which the stent 110 is laser cut after etching, grinding and other processing. But, embodiments of the stents disclosed herein are not necessarily limited to being laser-cut from a cylindrical tube with a predetermined wall thickness. They could also be formed or cut from flat sheets that are welded together at long edges to form a tube-like structure.

Each of the rings 112 is comprised of a plurality of ring struts 128 interconnected to form alternating peaks or apexes 120 and troughs 124. As shown in FIG. 8, each of the ring struts 128 is generally straight. In one embodiment shown in FIGS. 8-9, a stent 110 includes a plurality of rings 112 connected by a plurality of flexible connectors 132. The rings 112 are arranged in a spaced relationship along a long axis 116 of the stent 110. The connectors 132 extend between adjacent pairs of the rings 112. Each of the rings 112 and connectors 132 are comprised of a plurality of interconnecting struts. The dimensions and orientation of these struts are designed to provide flexibility and radial/crush stiffness according to principles of the present disclosure.

The exemplary hybrid stent 110 illustrated in FIG. 8 may be made of Nitinol tubing that is superelastic per ASTM F2063. The stent specification may further be as follows, post electropolishing: AF temperature of parts to be 19+/−10 degrees Celsius. The hybrid stent may be designed to treat a range of iliofemoral veins ranging in size from 12 mm to 20 mm. These dimensions are exemplary and a stent according to principles of the present disclosure are not so limited.

Figure 9A:
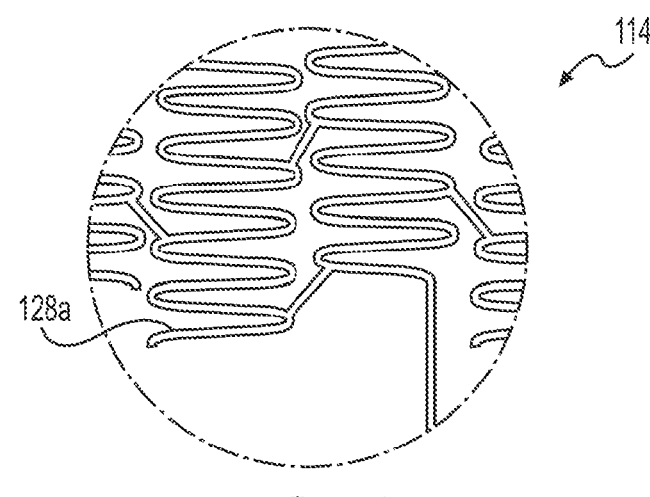
FIG. 9A, FIG. 9B and FIG. 9C illustrate details of the embodiment of FIG. 8.
Figure 9B:
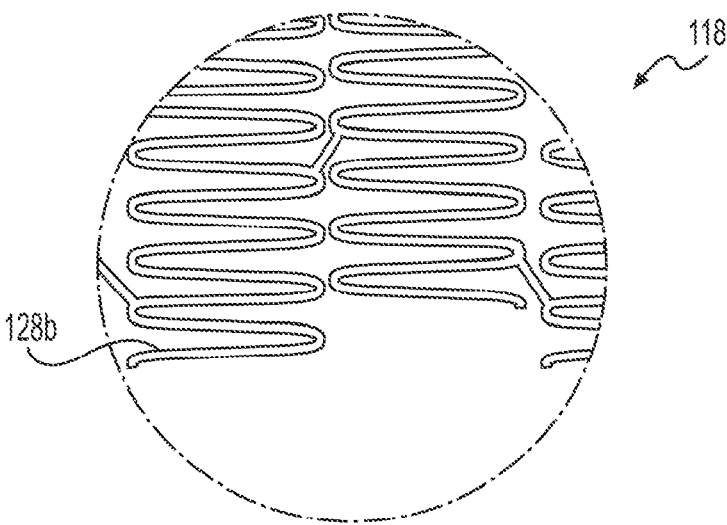
Figure 9C:
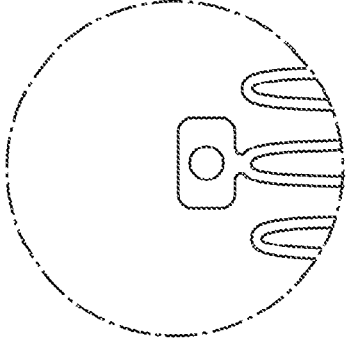

FIGS. 9A, 9B and 9C illustrate details of the strut and connector structure of the high radial/crush force segment 114 (FIG. 9A) and the highly flexible segment 118 (FIG. 9B) of the embodiment FIG. 8 at the locations indicated in FIG. 8. FIG. 9C is showing detailed dimensions of the eyelet 119 geometry in which a radiopaque (RO) marker will be inserted to aid the doctor with deployment location of the stent under fluoroscopy.

FIG. 9A illustrates ring struts 128a of the high radial/crush force segment 114. FIG. 9B illustrates ring struts 128b of the highly flexible segment 118.

As can be appreciated, foreshortening of the stent can be a particular problem for placement of a stent. In practice, stents with greater flexibility tend to foreshorten more. Accurate placement is ideal in all medical interventions, but it is of great interest in areas where the end that is first deployed is important. Such areas include at vessel bifurcations and branch vessels, so that the implant does not enter or interfere with the portion of the vessel that does not require treatment. Such a bifurcation is present at the inferior vena cava where it branches into right and left iliac veins, as described in more detail below.

Figure 10:
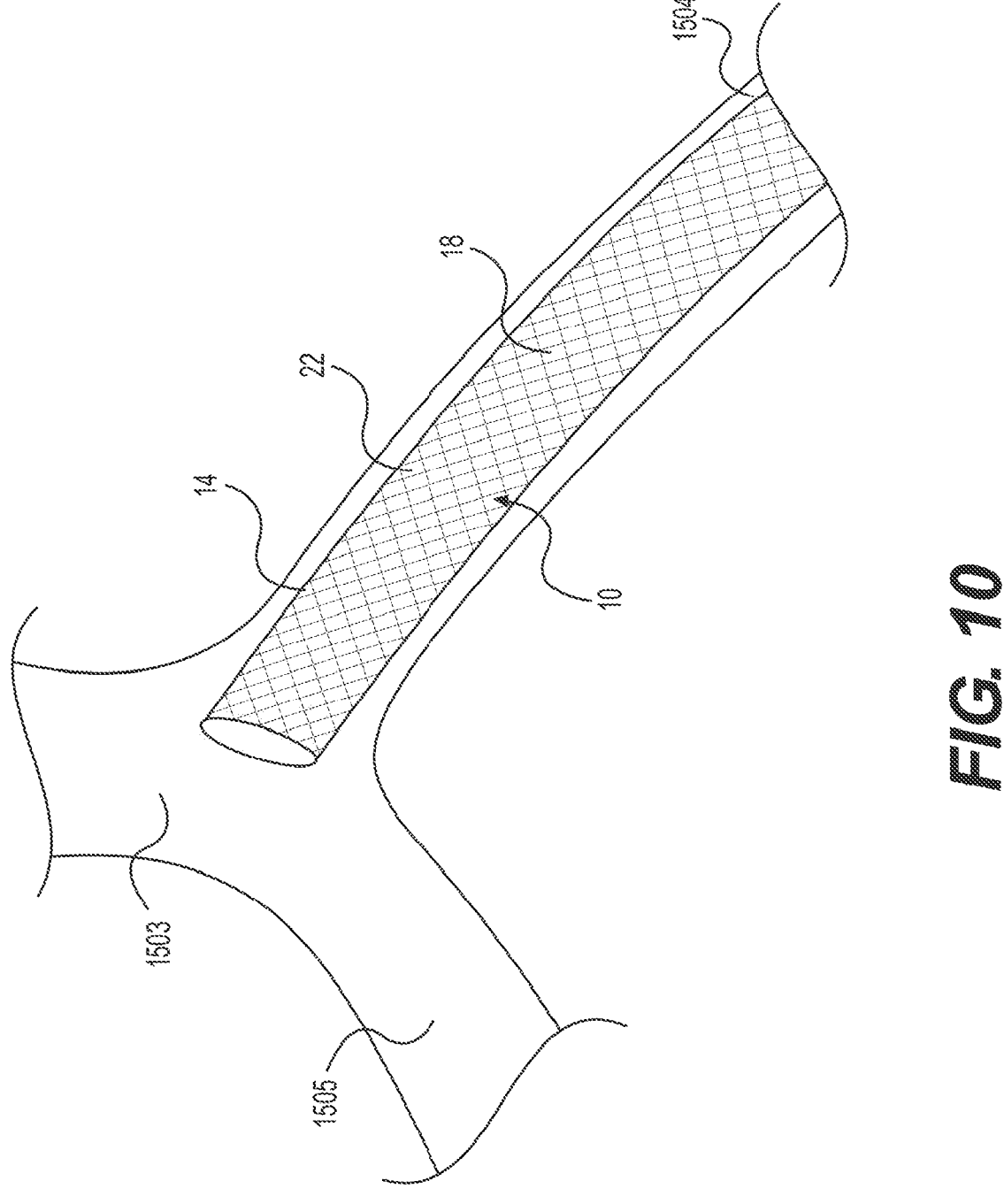
FIG. 10 illustrates an exemplary placement of a hybrid stent according to principles of the present disclosure in the left common iliac vein.

As described herein, a stent according to principles described herein includes a high radial/crush force segment and a highly flexible segment. The high radial/crush force segment, with its stiffer structure, will have minimal foreshortening, and as a result, can allow for more accurate placement in the vessel into which it is implanted. FIG. 10 illustrates a rough placement of a stent according to principles of the present disclosure. FIG. 10 illustrates the inferior vena cava 1503 branching into the left common iliac vein 1504 and right common iliac vein 1505. It will be understood that the rough diagram illustrated in FIG. 10 represents the view looking down on a patient laying face-up (i.e., an anterior-poster view of the patient at the location of the bifurcation of the inferior vena cava 1503). For sake of simplicity, the abdominal aorta and its branching are not shown in FIG. 10, but are shown in FIG. 2, above. In an aspect described herein, peak-trough configurations (e.g., if used with the highly flexible segment) may not appreciably foreshorten.

As illustrated in FIG. 10, a multi-segment stent 10 according to principles described is placed in the left common iliac vein 1504. The high radial force segment 14 of the stent 10 may be allowed to extend into the iliac vein 1503, although the end of the high radial force segment is intended to be placed to be at the junction of the left common iliac vein 1504 and the iliac vein 1503. The highly flexible segment 18 extends away from the high radial force segment 14 and the transition segment 22 between the highly flexible segment 18 and the high radial/crush force segment 14.

Figure 11:
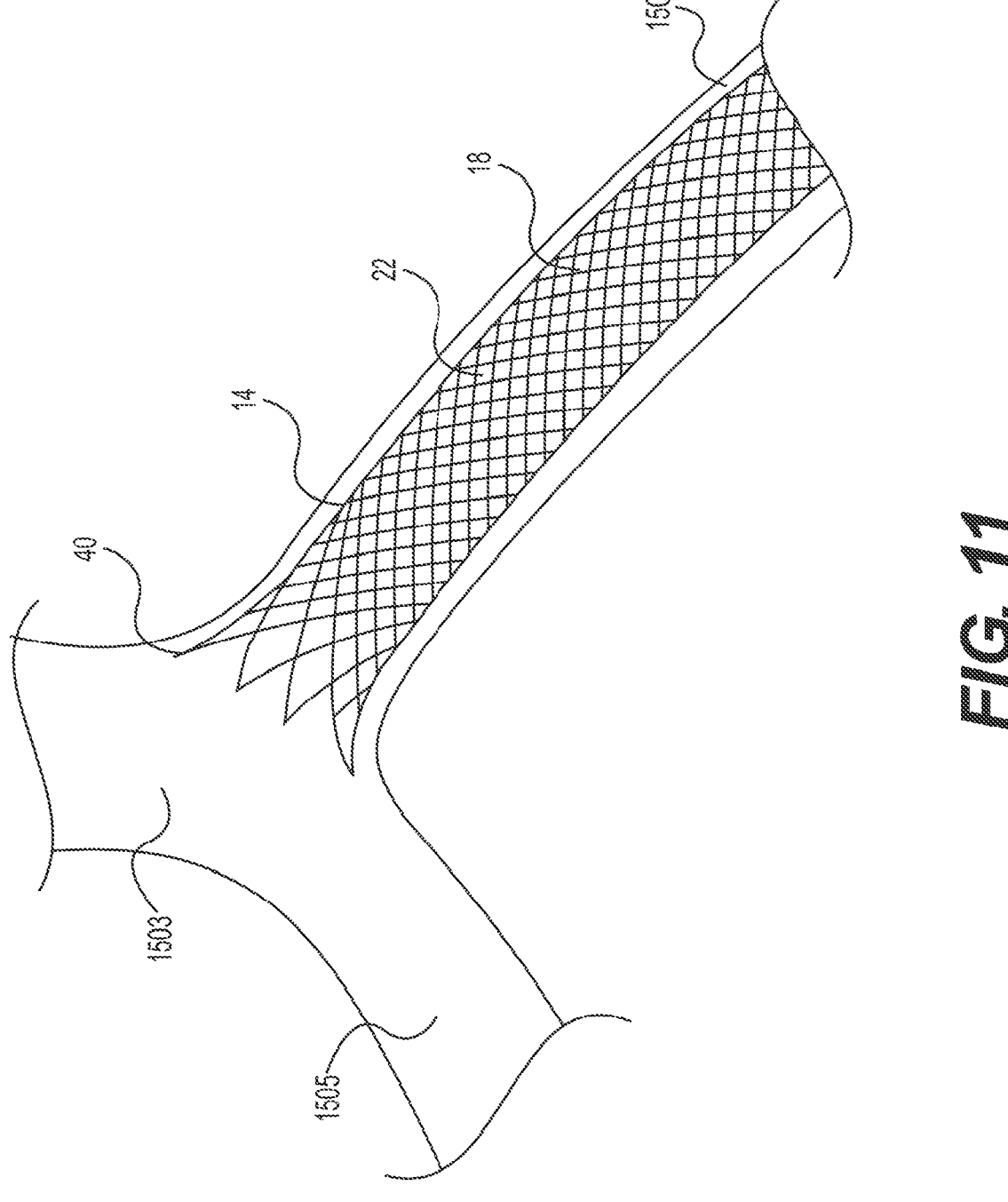
FIG. 11 illustrates an exemplary placement of a hybrid stent having a flared end according to principles of the present disclosure in the left common iliac vein.

To facilitate placement of the stent 10 at the junction of the left common iliac vein 1504 and the iliac vein 1503, the stent 10 may have a flared end 40 adjacent the high radial force segment 14, as illustrated in FIG. 11. The distal flared section is controlled by radius 'r'. Exemplary flare sizes include 2.5 mm×5.0 mm and 5.0 mm×5.0 mm, but stent flares according to principles of the present disclosure are not so limited. The flared distal end of the stent may be used for placement of the stent at a bifurcation of two vessels such as the common iliac vein 1504 and the iliac vein 1503. The pre-loaded stent configuration on the delivery system described herein allows the distal flared section of the stent to be partially deployed from the delivery system allowing the operator to position the flared section of the stent at the bifurcation of two vessels. The delivery catheter is advanced central to the vessel bifurcation to be treated, in this case the left common iliac vein 1504. If radiopaque markers are provided on the implant, the operator can seat the partially deployed flare section of the stent at the bifurcation junction using the radiopaque markers. Once the central flared end of the partially deployed stent is in the appropriate deployment location and seated at the bifurcation junction the remainder of the stent can be deployed.

Figure 12:
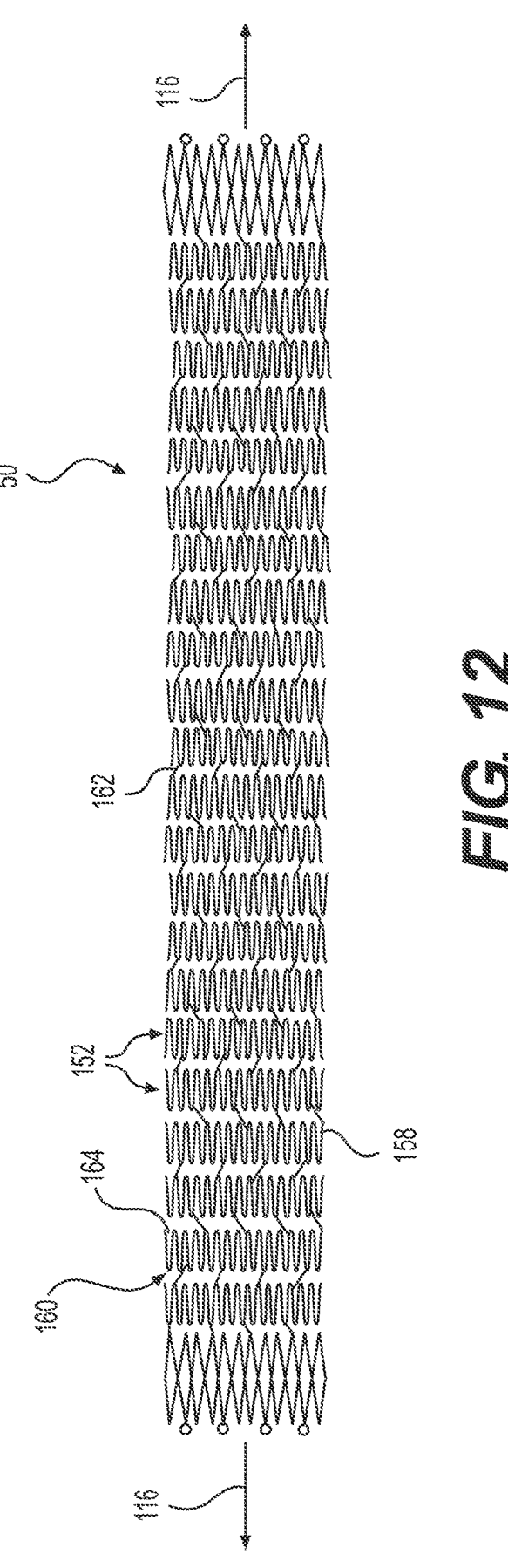
FIG. 12 illustrates an exemplary extension stent according principles of the present disclosure.

In an aspect of the present invention, a separate extension stent 50 may be included along with the stent 10. An embodiment of the separate extension stent 50 is illustrated in FIG. 12. As illustrated in FIG. 12, the separate extension stent 50 is tubular and may be a highly flexible segment similar to the highly flexible segment 18 in the hybrid stent 10 described above. In an aspect of the present disclosure, the separate extension stent 50 may comprise a plurality of rings 152, which comprise a plurality of ring struts 158 interconnected to form alternating peaks or apexes 160 and troughs 164. As shown in FIG. 12, each of the ring struts 158 is generally straight. The ring struts 158 may be connected to flexible connectors 162. The rings 152 are arranged in a spaced relationship along a long axis 116 of the stent 110. The flexible connectors 162 extend between adjacent pairs of the rings. The separate extension stent 50 may also include reinforcement rings on either or both ends of the tube. The dimensions and orientation of these struts are designed to provide flexibility and radial/crush stiffness according to principles of the present disclosure. Each of the rings 152 and connectors 162 comprises a plurality of interconnecting struts. The separate extension stent is made of an expandable material or a self-expandable material, such as Nitinol. The separate expansion stent 50 may be cut from a single tube, such as nitinol, for example, but could also be formed or cut from flat sheets that are welded together at long edges to form a tube-like structure.

Figure 13:
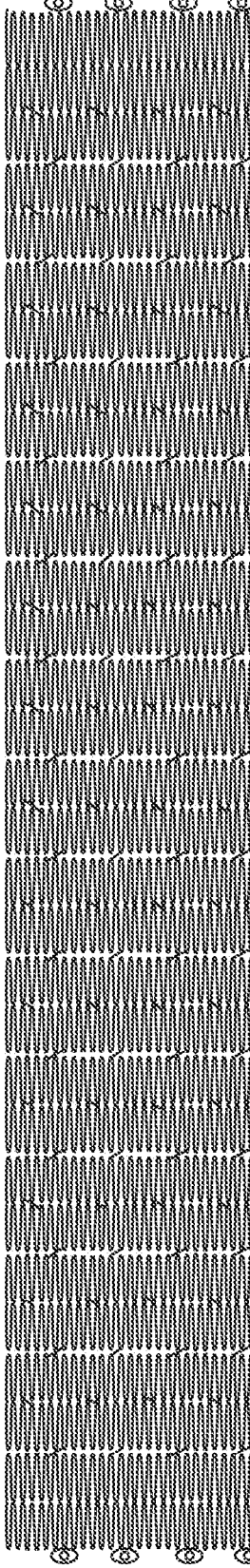
FIG. 13 illustrates an embodiment of an extension stent according to principles of the present disclosure.

An exemplary extension stent is illustrated in FIG. 13. The extension stent illustrated in FIG. 13 may be made of nitinol tubing that is superelastic per ASTM F2063. The stent specification may further be as follows, post electropolishing: AF temperature of parts to be 19+/−10 degrees Celsius. The extension stent may be designed to treat a range of iliofemoral veins ranging in size from 8 mm to 16 mm. These dimensions, as well as dimensions illustrated in the figures, are exemplary and a stent according to principles of the present disclosure are not so limited.

Figure 14:
FIG. 14 illustrates an exemplary placement of a hybrid stent and an extension stent according to principles of the present disclosure in the left common iliac vein.

The separate extension stent 50 is placed in the left iliac vein 1504 adjacent the highly flexible segment 18 of the hybrid stent 10 and may overlap the end of hybrid stent 10, as illustrated in FIG. 14. The region of overlap in the illustration is indicted by reference number 200. The placement of the hybrid stent 10 and the separate extension stent 50 may be performed using the same delivery device at the same time. A second delivery catheter with pre-crimped extension stent may be introduced into the treatment vessel and approximate the proximal end of the previously deployed hybrid stent. The catheter with crimped extension stent would be inserted into the proximal end of the hybrid stent, positioned and the stent would be deployed utilizing the radiopaque markers on both stents to achieve appropriate overlap, e.g., 1 cm. In another aspect, the extension stent can be implanted as a stand-alone stent.

It should be noted that an extension stent as described herein may be used in combination with other stents as a "main stent", besides the hybrid stent 10. In use, the extension stent can be used to allow for variation in placement.

In addition, the extension stent may include reinforcement rings where the reinforcement ring may be an area of greater stiffness/crush resistance at an end portion of the stent. "Greater stiffness" here means having a stiffness greater than a portion of the sent adjacent the reinforcement ring. The reinforcement ring having greater stiffness may provide good inflow into the stent and through the vessel having the implant therein. The reinforcement rings may make the extension stent easier to place with respect to the main stent, for example, by mitigating crushing of the ends as they are made to overlap. In addition, to facilitate placement, the ends of the extension stent and/or the stent to which it is to be placed adjacent can be coated with a polymer, such as urethane or PTFE. Also, the extension stent may include anchors, eyelets, radiopaque markers or other features to assist in placement of the extension stent. The extension stent may also be delivered with the main stent, or may be separately delivered to the vessel.

The extension stent may be delivered via an appropriate access site, (e.g. jugular, popliteal, etc.). The extension stent can be made to be "bidirectional", such that it could be preloaded onto a delivery catheter without specific regard to the direction of the delivery (e.g., jugular, popliteal, etc.). E.g. the delivery can be made from above the treatment region or from below the treatment region. Such bidirectionality can be facilitated by the extensions stent geometry being symmetrical such that ends of the extension stent have the same geometry. The stent may be delivered by a coaxial delivery catheter. In another aspect of the present disclosure, a novel delivery device may include a cartridge that may be loaded onto a catheter and the hybrid sent also loaded on the catheter. The cartridge can be flipped by the operator for retrograde or anterograde. The stent may be preloaded onto the delivery catheter for the direction of the delivery (e.g., jugular, popliteal, etc.)

As can be appreciated, the actual stent ring geometry may vary from that disclosed herein, as long as the stent 10 includes a first section with a relatively higher radial force or crush resistance than a second section of the stent that has a relatively higher flexibility than the first section. It is also contemplated that the separate extension stent 50 have a flexibility similar to the highly flexible segment of the hybrid stent 10. Exemplary stent geometries for segments of the hybrid stent 10 and the extension stent 50 are taught in U.S. patent application Ser. Nos. 15/471,980 and 15/684, 626, which are hereby incorporated by reference for all purposes as if fully set forth herein.

Figures 15A, 15B:
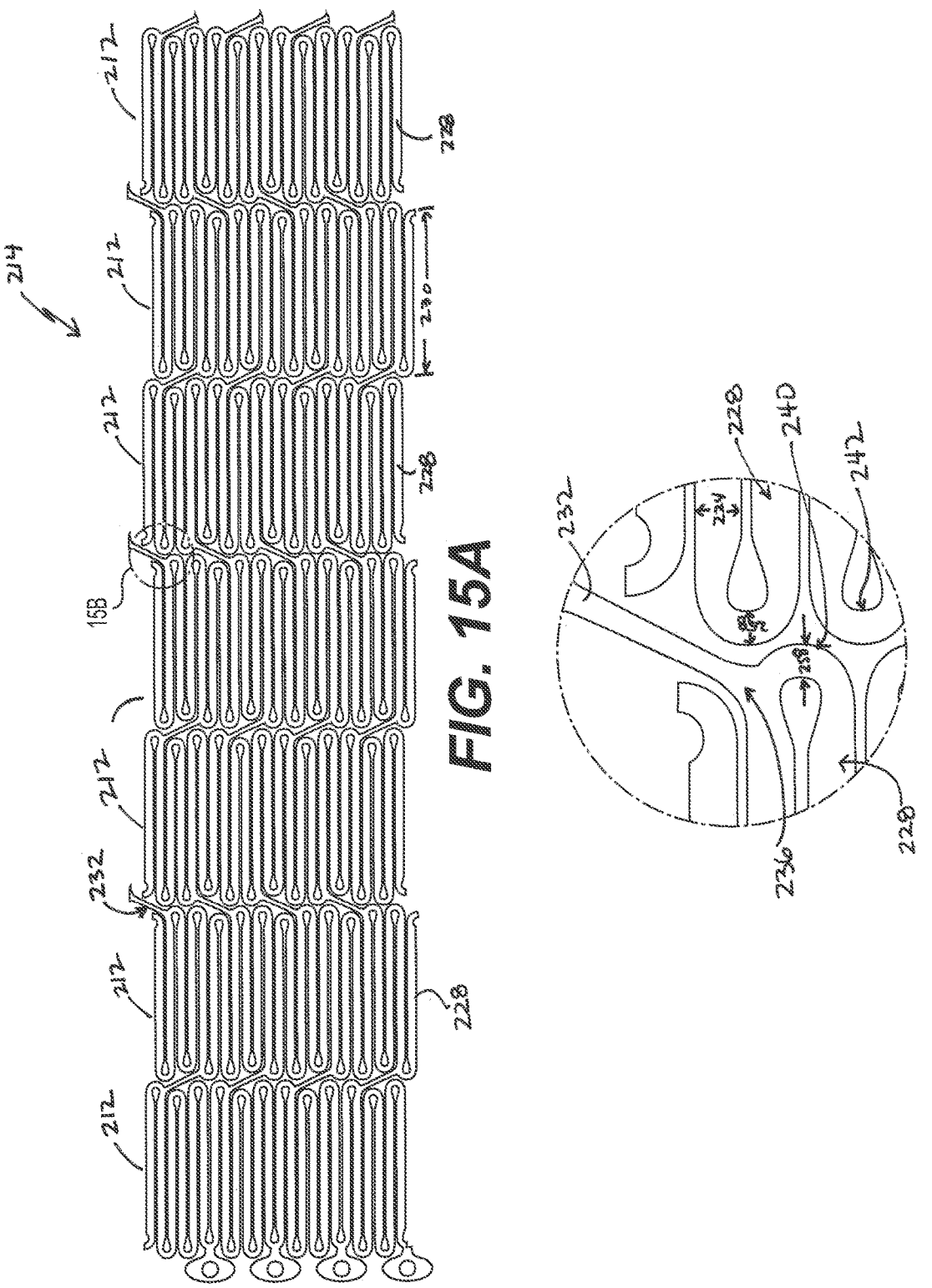
FIGS. 15A and 15B illustrate a planar/flattened view of an exemplary embodiment of a high radial/crush force segment of a stent in a compressed state according to principles of the present disclosure.

FIGS. 15A and 15B illustrate a "cut" (planar/flattened) view of an exemplary embodiment of a high radial/crush force segment of a stent in a compressed state according to principles of the present disclosure. FIG. 15A illustrates a stent geometry for the high radial/crush force segment 214 of a stent according to principles described herein. FIGS. 15A and 15B illustrate the exemplary high radial/crush force segment in a compressed state. FIG. 15B illustrates a magnified view of apices of the high radial/crush force segment of the embodiment illustrated in FIG. 15A according to principles of the present disclosure. The exemplary high radial/crush force segment 214 includes a plurality of rings 212 connected by a plurality of connectors 232. The rings 212 are arranged in a spaced relationship along a long axis of the stent high radial/crush force segment 214. The connectors 232 extend between adjacent pairs of rings 212. Each of the rings 212 is comprised of a plurality of interconnecting struts 228. The dimensions and orientation of these struts are designed to provide a relatively high radial/crush force such that the stent segment has a higher crush resistance than the adjacent transition segment or the highly flexible segment, (see FIGS. 6 and 8).

Each of the rings 212 is comprised of a plurality of ring struts 228 interconnected to form alternating peaks or apexes 240 and troughs 242. As shown in FIGS. 15A and 15B, each of the ring struts 228 is generally straight and has a main strut width 224 and a strut length 230. The main strut width 224 is the width of the strut in the circumferential direction but adjusted to be at about a right angle to the edge of the strut. In other words, the main strut width 224 is an edge to edge measurement corresponding to the outermost circumferential surface of the struts of the rings 212

Each of the connectors 232 itself is comprised a connector strut 234. In the present embodiment, the connector is a single connector strut 234, but the connector design is not necessarily limited to a single strut. As illustrated in FIG. 15A, an end 236 of each connector strut 234 connects to a respective ring strut 228. Each connector strut 234 in a plurality extends from its end that is connected to the respective ring strut 228 in a respective ring 212 toward an adjacent ring 212. The connector strut 234 extends in a direction neither parallel nor perpendicular to the longitudinal axis of the stent high radial/crush force segment 214. As illustrated in FIG. 15A, in this aspect of the high radial force segment in the illustrated embodiment, the connector connects 232 to a ring strut 228 in an adjacent ring that is offset in a latitudinal direction from the ring strut from which it extends. That is, as illustrated, the connector 234 connect from a ring strut 228 to a ring strut two places over from the one immediately adjacent—in the illustrated embodiment, there are two unconnected apices between two connected apices. In other words, in some embodiments, each ring strut 228 is not necessarily connected to another ring strut in an adjacent ring by a connector. It is possible, in another aspect, for each apex 240 to connect to an apex 240 in an adjacent ring 212. In some instances, those apices 240 may be connected by a connector 232 whose connection thereto is offset from the actual peak of the apex 240, as illustrated in detail in FIG. 15B. In some embodiments, the connectors 232 do not connect directly to or at the apexes 240 of the rings 212. Instead, they are offset somewhat along the length of the ring struts 228 to which they are connected. Also, in some embodiments, as illustrated in FIG. 15A, connectors 232 on either side of a ring 212 are "wound" in opposite directions (e.g., clockwise and counter clockwise directions) in a compressed configuration.

The connector struts 234—similar to the ring struts 228 of the exemplary embodiment—have a relatively constant width except where they connect to the rings 212. As with the ring struts 228 described above, the width of the connector struts 234 may enlarge somewhat as they merge into connections with the rings 212. As shown in FIG. 15B, for example, each of the connectors 232 also includes a main connector width 256 (between arrows) and an apex connector width 258 (between arrows). The main connector width 256 is the width of the connector strut 228, usually the minimum width or width expressing the area of highest flexibility, of the strut between the rings 212 and the connector apex 240. The apex connector width 258 is the width of the connector apex 240 somewhere along its bend, such as in the middle of the bend. In any case, the apex connector width 258 can be a structural expression of an area of high flexibility on the connector apex 240.

Figure 16:
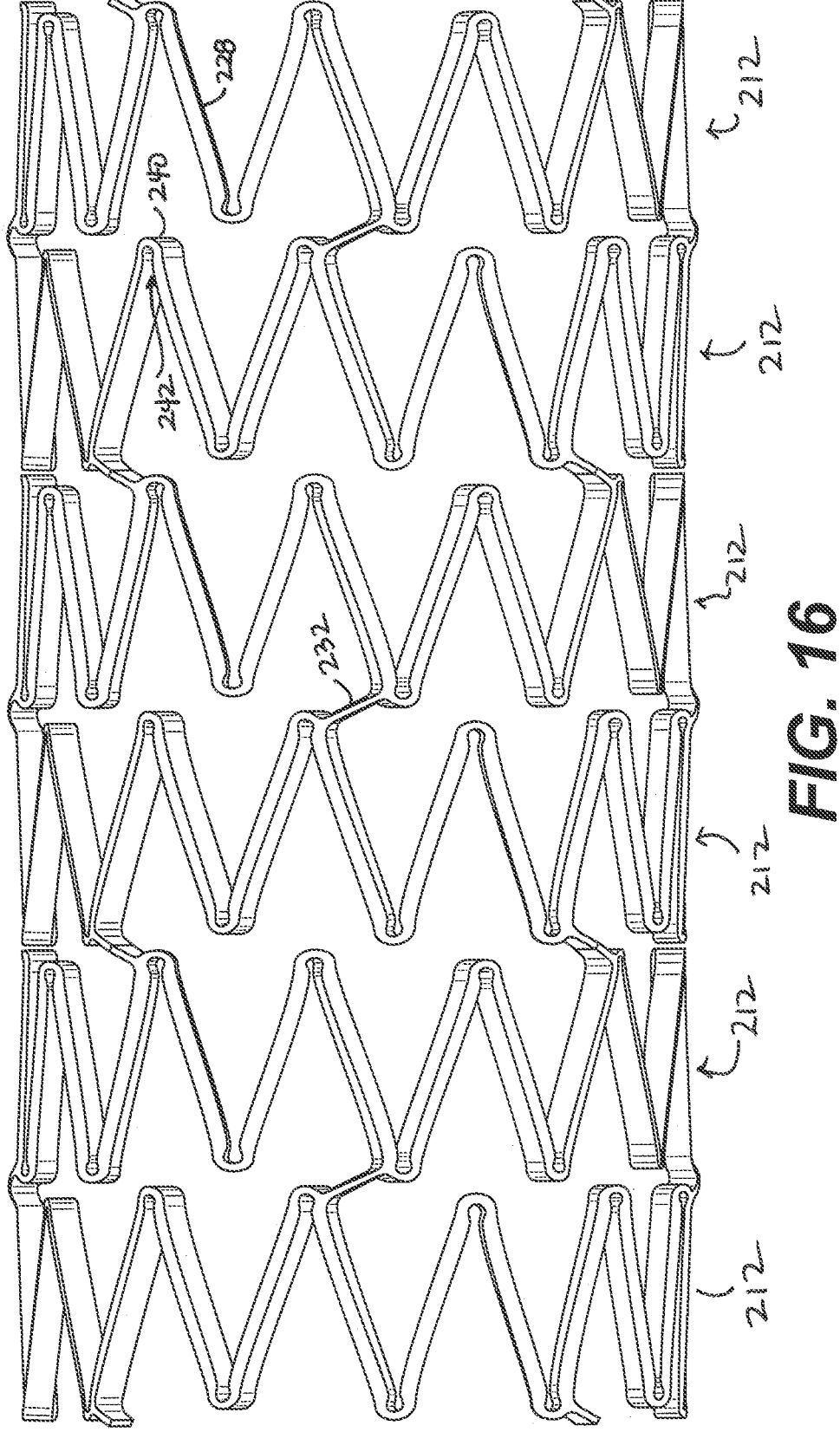
FIG. 16 illustrates an exemplary embodiment of a high radial/crush force segment of a stent in an expanded state according to principles of the present disclosure.

FIG. 16 illustrates an exemplary embodiment of a high radial/crush force segment of a stent in an expanded state according to principles of the present disclosure. As illustrated in FIG. 16, upon expansion of the compressed high radial force segment 228 illustrated in FIG. 15A, the rings 212 rotate such that the apexes of each ring 212 is circumferentially aligned between the apexes of the adjacent ring 212, through the design of the length of the connectors 232. In some embodiments, such as larger stents (e.g., outer diameters in the approximate range of 16-20 mm) the flexible connectors between and MTS section and a transition section may have "straight" connectors (in an expanded state), e.g. extending substantially in the axial direction of the stent. In other embodiments, such as smaller stents (e.g. outer diameters in the approximate range of 12-14 mm) may have angled stents in an expanded state, e.g. extending in a direction not substantially in the axial direction of the stent. While these embodiments are mentioned here, it is possible that any size stent may have "straight" connectors and/or "angled" connectors in the expanded state.

Figures 17A, 17B, 17C:
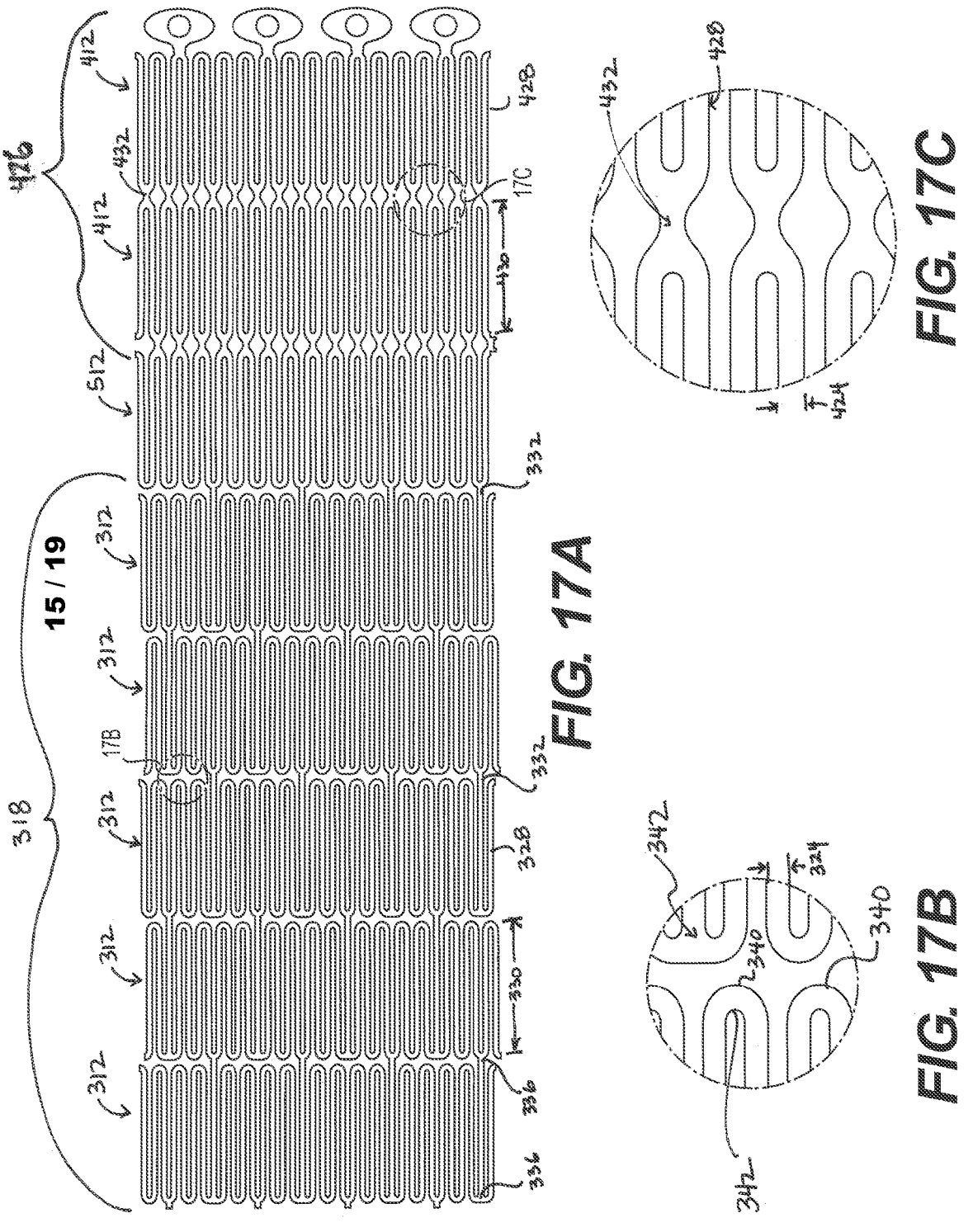
FIGS. 17A, 17B and 17C illustrate a planar/flattened view of an exemplary embodiment of a highly flexible segment of a stent in a compressed state according to principles of the present disclosure.

FIG. 17A illustrates a planar/flattened view of an exemplary embodiment of a flexible segment and an exemplary embodiment of a reinforcement segment of a stent in a compressed state according to principles of the present disclosure. FIG. 17B illustrates a magnified view of apices of the flexible segment of the embodiment illustrated in FIG. 17A according to principles of the present disclosure. FIG. 17C illustrates a magnified view of apices of the reinforcement rings of the embodiment illustrated in FIG. 17A according to principles of the present disclosure.

As illustrated in FIG. 17A, the exemplary flexible segment 318 includes a plurality of rings 312 connected by a plurality of connectors 332. The rings 312 are arranged in a spaced relationship along a long axis of the stent flexible segment 318. The connectors 332 extend between adjacent pairs of rings 312. Each of the rings 312 is comprised of a plurality of interconnecting struts 328. The dimensions and orientation of these struts are designed to provide a relatively higher flexibility such that the stent segment has a greater flexibility than the adjacent transition segment or the high radial/crush force segment, (see FIGS. 6 and 8).

Each of the rings 312 is comprised of a plurality of ring struts 328 interconnected to form alternating peaks or apexes 340 and troughs 342. As shown in FIGS. 17A and 17B, each of the ring struts 328 is generally straight and has a main strut width 324 and a strut length 330. The main strut width 324 is the width of the strut in the circumferential direction but adjusted to be at about a right angle to the edge of the strut. In other words, the main strut width 324 is an edge to edge measurement corresponding to the outermost circumferential surface of the struts of the rings 312

Each of the connectors 332 itself is comprised a connector strut 334. In the present embodiment, the connector 332 is a single connector strut 334, but the connector design is not necessarily limited to a single strut. As illustrated in FIG. 17A, an end 336 of each connector strut 334 extends from a trough 342 to an apex in an adjacent ring 312. In the exemplary embodiment, the connector strut 334 extends in a direction substantially parallel to the longitudinal axis of the stent flexible segment 318. As illustrated in FIG. 17A, in this aspect of the flexible segment in the illustrated embodiment, every fourth trough 342 is connected by a connector 332 to an apex 340 in an adjacent ring 312. That is, as illustrated, three adjacent troughs are not connected to the adjacent ring by a connector 332. In other words, in some embodiments, each trough is not necessarily connected to an apex 340 in an adjacent ring by a connector. It is possible, in another aspect, for each trough 342 to connect to an apex 340 in an adjacent ring 312. In some embodiments, although not shown, the connectors 332 may not connect directly to or at troughs 342 or the apexes 340 of the rings 312. Instead, they are offset somewhat along the length of the ring struts 328 to which they are connected. Also, in some embodiments, as illustrated in FIG. 15A, connectors 332 on either side of a ring 212 are "wound" in opposite directions (e.g., clockwise and counter clockwise directions).

Figure 18:
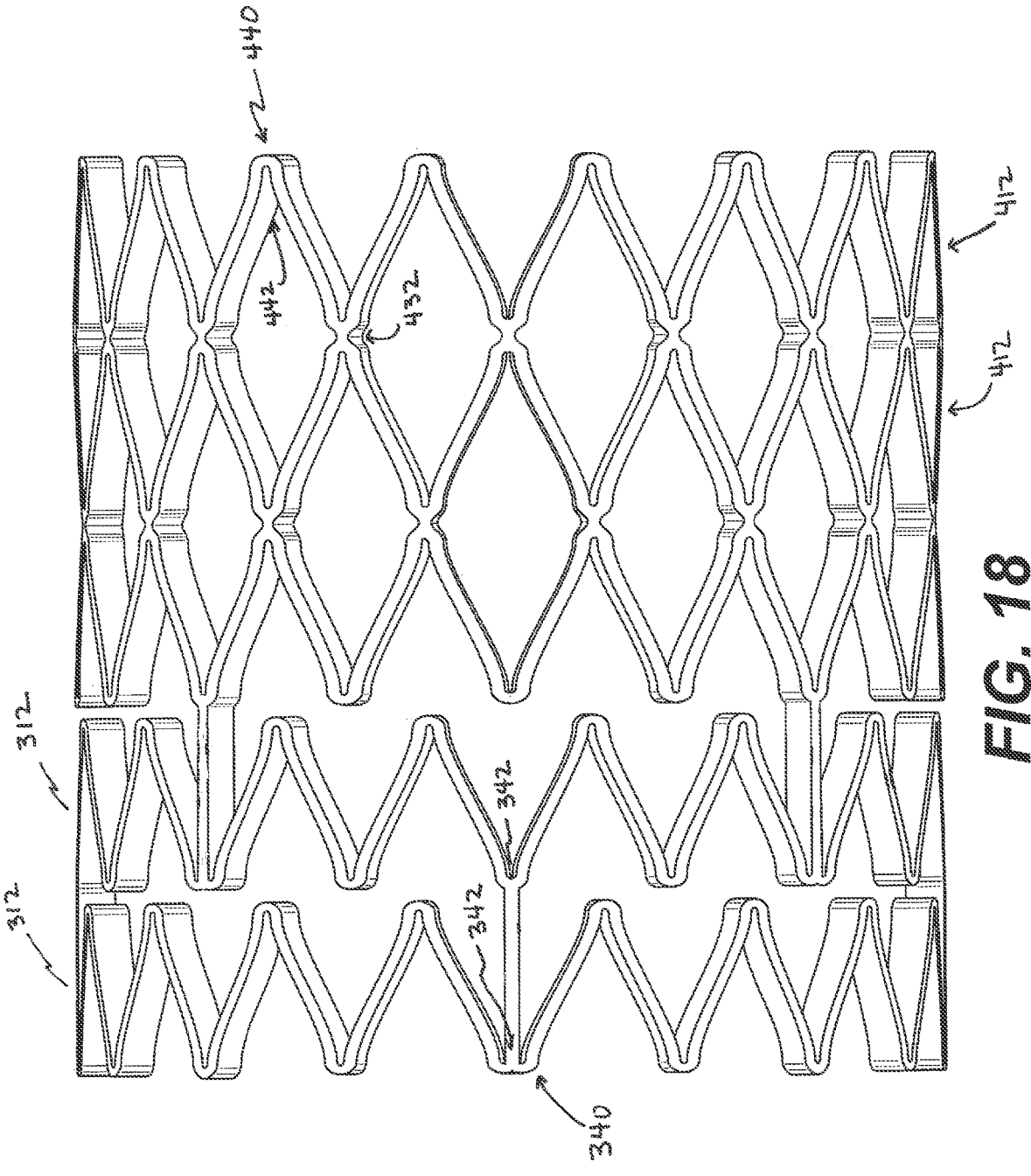
FIG. 18 illustrates an exemplary embodiment of a highly flexible segment of a stent in an expanded state according to principles of the present disclosure.

The connector struts 334—similar to the ring struts 328 of the exemplary embodiment—have a relatively constant width except where they connect to the rings 312. The width of the connector struts 334 may enlarge somewhat as they merge into connections with the rings 312. FIG. 18 illustrates an exemplary embodiment of a flexible segment 318 of a stent in an expanded state according to principles of the present disclosure.

Figure 21:
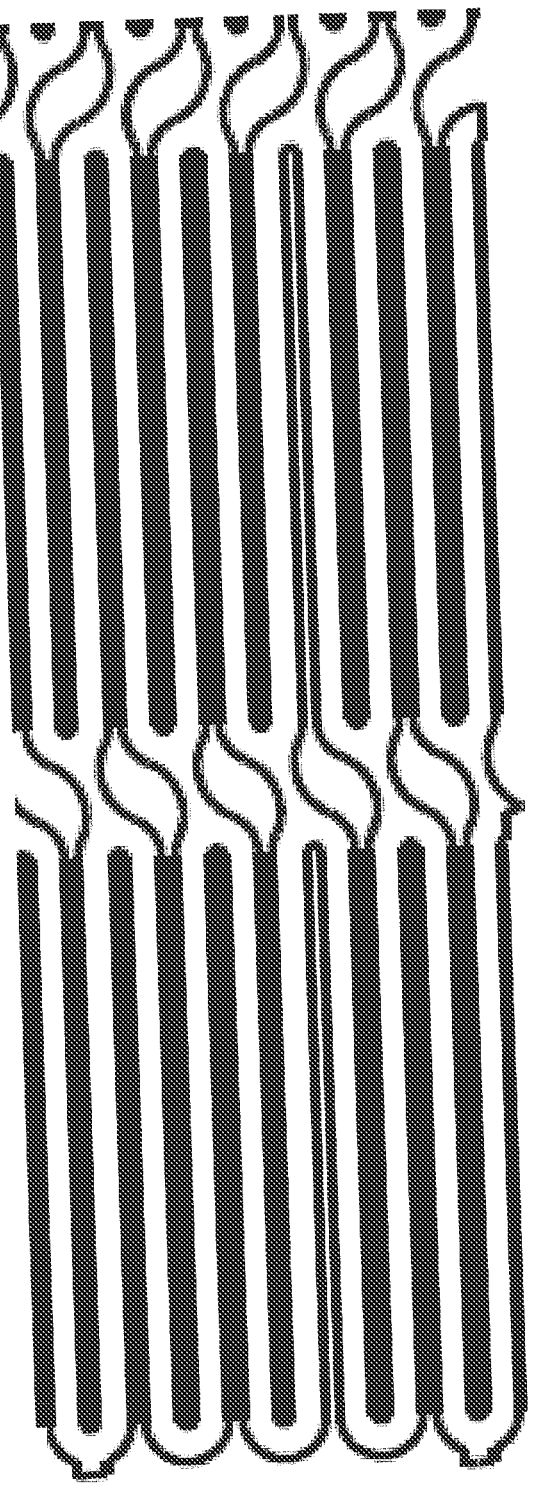
FIG. 21 illustrates an embodiment of connectors extending between connectors at points spaced from the apices of the connector.

The exemplary reinforcement ring segment 426 includes a plurality of rings 412 connected by a plurality of connectors 432. The rings 412 are arranged in a spaced relationship along a long axis of the reinforcement rings 426. The connectors 432 extend between adjacent pairs of rings 412. Each of the rings 412 is comprised of a plurality of interconnecting struts 428. The dimensions and orientation of these struts are designed to provide a relatively greater radial force such that the stent segment has a higher crush resistance than the adjacent transition segment or the highly flexible segment, (see FIGS. 6 and 8). The present figures illustrate connectors 432 as horizontal with/parallel to the stent axial direction, but they could also be angled, and adjacent rings can be orientated such that apex-apex between rings are not aligned, as illustrated in FIG. 21. This connection pattern may be used at the end rings of the extension stent 50.

Each of the rings 412 is comprised of a plurality of ring struts 428 interconnected to form alternating peaks or apexes 440 and troughs 442. As shown in FIGS. 17A and 17C, each of the ring struts 428 is generally straight and has a main strut width 424 and a strut length 430. The main strut width 424 is the width of the strut in the circumferential direction but adjusted to be at about a right angle to the edge of the strut. In other words, the main strut width 424 is an edge to edge measurement corresponding to the outermost circumferential surface of the struts of the rings 312

Each of the connectors 432 itself may be comprised of a connector strut 434. In the present embodiment, the connector 432 is a single connector strut 434, but the connector design is not necessarily limited to a single strut. As illustrated in FIG. 17A, an end 436 of each connector strut 432 extends from an apex 440 to an apex 440 in an adjacent ring 412. In the exemplary embodiment, the connector 432 extends in a direction substantially parallel to the longitudinal axis of the stent reinforcement ring 412. As illustrated in FIG. 17A, in this aspect of the reinforcement segment 426 in the illustrated embodiment, every apex 440 is connected by a connector 432 to an apex 440 in an adjacent ring 412. In other words, in some embodiments, each apex is connected to an apex 440 in an adjacent ring by a connector 432. It is possible, in another aspect, for not all apices 440 to connect to an apex 440 in an adjacent ring 412. In some embodiments, although not shown, the connectors 432 may not connect directly to or at apexes 440 of the rings 412. Instead, they are offset somewhat along the length of the ring struts 428 to which they are connected.

The connector 432—similar to the ring struts 428 of the exemplary embodiment—have a relatively constant width except where they connect to the rings 412. The width of the connector struts 432 may enlarge somewhat as they merge into connections with the rings 412 or ring apices 440. FIG. 18 illustrates an exemplary embodiment of the reinforcement ring segment 426 of a stent in an expanded state according to principles of the present disclosure.

FIG. 17A also illustrates a transition portion where the flexible segment 318 connects to the reinforcement segment 426. As illustrated by the connection of the third ring from the right 512 in FIG. 17A, a connector 332 extends from a trough 340 from a ring 312 of the flexible segment 318 and connects to an apex 540a in the adjacent ring 512 (second ring from the right in FIG. 17A). On the opposite side of ring 512, each apex 540b of the ring 512 connects to apices 440 in adjacent ring 412. Accordingly, transition between the flexible segment 318 to the reinforcement segment 426 is accomplished.

Figure 19:
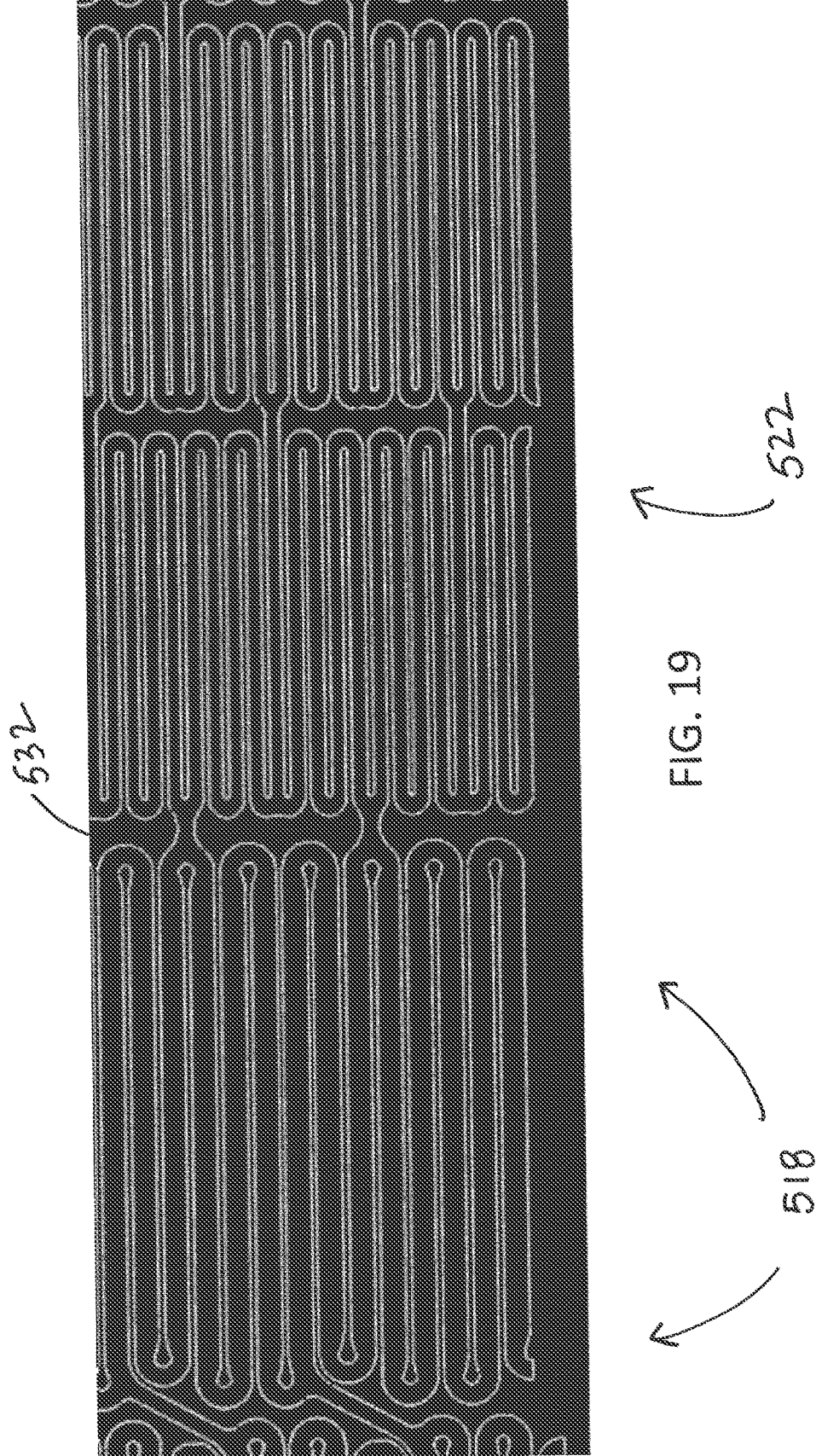
FIG. 19 illustrates a transition area between two segments of a hybrid stent according to principles described herein.

A hybrid stent 510 having separate segments of varying radial/crush force and flexibility according to principles described herein may benefit from a smooth transition between segments. In an aspect of the present hybrid stent, the high radial/crush force segment may include rings along the length of the stent that are designed to rotate with respect to one another, and the transition and flexible region, where the stent opens more uniformly, may have no rotation. Thus, an aspect may allow for smooth transition between two adjacent regions/segments of the stent to address crimp and deployment issues that may result from the twist of the last ring of the high radial/crush force segment creating a twist in the adjacent transition/flexible segment region. FIG. 19 illustrates an embodiment of transitions between segments that enable a segment that has rotating/twisting rings when being collapsed/crimped or during expansion when being deployed to be connected to a segment that does not twist but has additional means of being flexible. FIG. 19 illustrates straight connection transition from a rotating segment (left) of, e.g., a high radial force segment 518, to a non-rotating segment (right), e.g. a transition segment 522. The straight connection in the exemplary embodiment includes a plurality of straight connectors 532. The straight connection at that junction enables a uniform crimp and reduces or eliminates the twisting and crimping issues.

Figure 20:
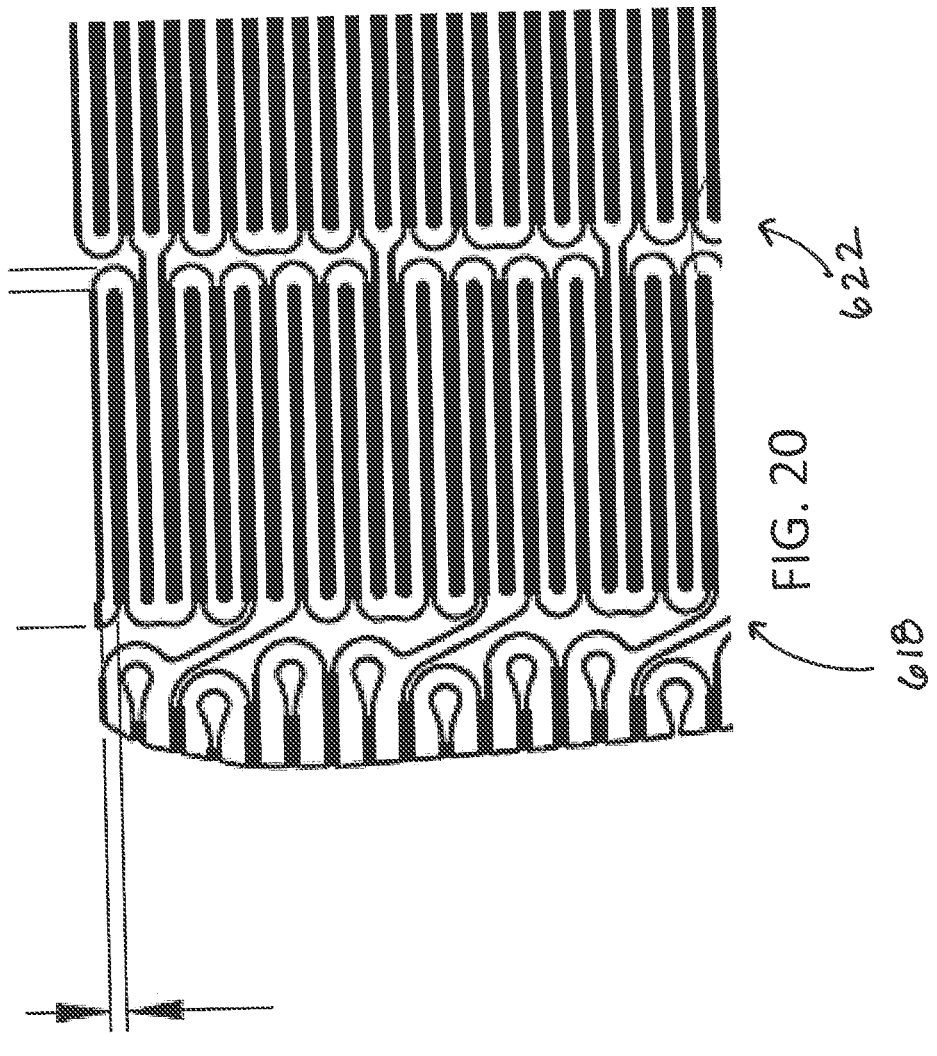
FIG. 20 illustrates an exemplary connection between a high radial force segment and a transition section according to principles described herein.

FIG. 20 illustrates an exemplary connection between a high radial force segment (MTS segment) (left) 618 and a transition section (right) 622 according to principles described herein that may be applicable in smaller hybrid stents, such 12-14 mm stents. The illustrated connection and each respective illustrated segment is but one stent geometry.

It is noted that the struts of the rings and flexible connectors with structure, including areas of expanded or reduced width or thickness, to account for venous applications, may be used. As another example, it is noted that venous applications benefit from configurations that improve flexibility (due to the greater elasticity of venous applications) while maintaining enough stiffness to resist pressure on the venous structure in selected areas (such as for the May-Thurner syndrome).

Notably the stents herein are not necessarily limited to venous applications unless specifically required by the claims. The disclosed stents could be employed in arterial and biliary applications, for example. But, are particularly suited for the demands of relatively soft structures defining lumens that are subject to much greater bending, twisting, stretching and other contortions and loads than are general arterial lumens.

To deploy the implant, the implant may be radially compressed/crimped to a smaller diameter for loading onto/into a delivery catheter. The implant may be crimped over a balloon on the inner core of the delivery system which may be later inflated to expand the crimped implant to the desired diameter.

Implants such as those described above may advantageously provide an adaptive diameter and/or flexibility to conform the dynamic movement of peripheral veins in leg/pelvis thereby facilitating treatment of both iliac vein compression syndrome and iliofemoral venous outflow obstructions.

It may be desirable to have a stent that will conform to the existing path of a vein instead of a straightening out of the vessel by the stent. It may also be desirable to have a high radial/crush stiffness of the stent to resist collapse of the stent under crushing load and to maximize the resultant diameter of the treated vessel at the location of the stent deployment. With most stent constructions there is a direct relationship between radial stiffness and axial stiffness.

Common commercially available balloon expandable stents experience a dramatic change in length as a balloon is used to expand the stent within the vessel. Common commercially available self-expanding stents experience a change in length less dramatic, but still substantial, which increases with increasing stent length. Change in length between the configuration within the delivery system and when deployed in the vessel causes difficulty in placing/landing the stent precisely at the target location. When the stent is delivered in its crimped configuration, then deployed or expanded, the shortening in length causes the stent target deployment location to have to offset from the target dwell location. The magnitude of this effect is not controllable or easily anticipated as it is dependent on the luminal cross-section along the length of the target dwell location (which is frequently and unexpectedly influenced by residual stenosis, irregular shape due to external objects, and/or forces, etc.). For target lesions leading up to the junction of the left and right iliac into the IVC, this causes difficulty in placing the stent to dwell completely within the iliac along its total length up to the junction to the inferior vena cava without crossing into the inferior vena cava. Placement of a high radial/crush force segment at the junction not only assists in addressing crush by May-Thurner Syndrome, but also may assist in reducing foreshortening from the target location.

Embodiments disclosed herein can be used for both balloon expandable and self-expanding stent designs. The stent designs can be used for all stent interventions, including coronary, peripheral, carotid, neuro, biliary and, especially, venous applications. Additionally, this could be beneficial for stent grafts, percutaneous valves, etc.

Currently available implants are typically loaded and retained onto a delivery system in a crimped configuration and then navigated and deployed in the desired anatomical location where they expand to the implanted configuration. The final implanted configuration can be achieved through mechanical expansion/actuation (e.g., balloon-expandable) or self-expansion (e.g., Nitinol). Self-expanding implants are manufactured from super elastic or shape memory alloy materials. Accurate and precise deployment of a self-expanding implant can be challenging due to a number of inherent design attributes associated with self-expanding implants. The implant may jump/advance from the distal end of the delivery system during deployment due to the stored elastic energy of the material. Additionally, the implant may foreshorten during deployment due to the change in the implant diameter from the crimped configuration to the expanded configuration. Finally, physiological and anatomical configurations, such a placement at or near bifurcations of body lumens, can affect accurate placement of implants. Once the implant is placed within the body lumen there is potential for uneven expansion or lack of circumferential implant apposition to the body lumen which can result in movement, migration or in certain severe cases implant embolization.

In some embodiments, a self-expanding implant designed with sufficient radial force or crush resistance to resist constant compression of the body lumen while providing optimal fatigue resistance, accurate placement, and in-vivo anchoring to prevent movement/migration is provided. Additionally, various methods for deployment and implantation for treating iliac vein compression syndrome and venous insufficiency disease are provided.

In some embodiments, the implant comprises a purposely designed venous implant intended to focally treat iliac vein compression (May-Thurner Syndrome). The implant may be relatively short in length (~60 mm) and may be manufactured from self-expending Nitinol with integrated anchor features to aid in accurate placement and to mitigate migration following implantation. The implant and delivery system are designed for precise deployment and placement at the bifurcation of the inferior vena cava into the right and left common iliac veins.

As another feature, the stents disclosed herein can include anchor members, radiopaque markers, or eyelets, for example, set forth in pending U.S. patent application Ser. Nos. 15/471,980 and 15/684,626, which are hereby incorporated by reference for all purposes as if fully set forth herein.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments but should be defined only in accordance with the following claims and their equivalents.

What is claimed is:

1. A stent, comprising:
a first stent segment comprising a plurality of first rings connected to one another to form a series of said first rings, the first rings comprising: a plurality of first ring struts connected such that each of the plurality of first rings comprises a sinusoidal pattern having a plurality of apices and troughs, each first ring connected to an adjacent first ring by at least one connector, the connector extending from a ring strut of the first ring from a position offset from an apex of said first ring to a ring strut of the adjacent first rings offset from an apex of the adjacent ring, a second stent segment comprising a plurality of second rings connected to one another to form a series of said second rings wherein: the second stent segment is coupled to the first stent segment;

said first stent segment has a first stiffness and a first chronic outward force and the second stent segment has a second stiffness and a second chronic outward force, wherein the first stiffness is different from the second stiffness and the first chronic outward force is different from the second chronic outward force.

2. The stent of claim 1, further comprising at least one reinforcement ring coupled to one of the first rings or one of the second rings, such that the at least one reinforcement ring is the end ring of said stent, the reinforcement ring having a third stiffness and a third chronic outward force, where the third stiffness is different from the first stiffness and the second stiffness and the third chronic outward force is different from the first chronic outward force and the second chronic outward force.

3. The stent of claim 1, wherein the first stent segment and the second stent segment have substantially the same diameter in an expanded state.

4. The stent of claim 2, wherein the first stent segment, the second stent segment and the reinforcement ring have substantially the same diameter in an expanded state.

5. The stent of claim 1, the second rings comprising: a plurality of second ring struts connected such that each of the plurality of second rings comprises a sinusoidal pattern having a plurality of apices and troughs, each second ring connected to an adjacent second ring by at least one connector, the connector extending from a trough of the second ring to an apex of the adjacent second ring.

6. The stent of claim 1, wherein each first ring is connected to the adjacent ring by a number of connectors fewer than the number of apices of each first ring.

7. The stent of claim 1, wherein the at least one connector extends in a direction non-parallel to a longitudinal axis of the first stent segment.

8. The stent of claim 7, wherein the at least one connector extends past at least one apex of the adjacent ring to a connection point on the ring strut of the adjacent first ring in a compressed configuration.

9. The stent of claim 7, wherein connectors on either side of a first ring are wound in opposite directions in a compressed configuration.

10. The stent of claim 2, wherein at least one reinforcement ring comprising a plurality of reinforcement ring struts connected such that the at least one reinforcement ring comprises a sinusoidal pattering having a plurality of apices and troughs, and further comprising an additional reinforcement ring connected to the at least one reinforcement ring by a reinforcement connector, wherein the reinforcement connector extends from an apex of the at least one reinforcement ring to an apex of the additional reinforcement ring.

11. The stent of claim 10, wherein each apex of the at least one reinforcement ring is connected to the additional reinforcement ring by a reinforcement connector.

12. The stent of claim 1, wherein the second stent segment is coupled to the first stent segment by a substantially straight connector connecting one of the plurality of second rings to an adjacent one of the plurality of first rings.

13. The stent of claim 12, the second rings comprising: a plurality of second ring struts connected such that each of the plurality of second rings comprises a sinusoidal pattern having a plurality of apices and troughs and wherein an apex of the adjacent one of the plurality of first rings is connected by the substantially straight connector to an apex of the one of the plurality of second rings.

14. The stent of claim 13, wherein a plurality of apices of the adjacent one of the plurality of first rings are connected to a plurality of apices of the one of the plurality of second rings, each apex of the adjacent one of the plurality of first rings connected to a respective one of the plurality of apexes of the one of the plurality of second rings by the substantially straight connector.

15. The stent of claim 14, wherein the plurality of apices of the adjacent one of the plurality of first rings is fewer than all of the apices of the adjacent one of the plurality of first rings.

16. The stent of claim 14, wherein the plurality of apices of the one of the plurality of second rings is fewer than all of the apices of the one of the plurality of second rings.

17. The stent of claim 13, wherein each connected apex of the adjacent one of the plurality of first rings is spaced from another connected apex of the adjacent one of the plurality of first rings by an apex of the adjacent one of the plurality of first rings that is not connected to the one of the plurality of second rings.

18. The stent of claim 13, wherein each connected apex of the one of the plurality of second rings is spaced from another connected apex of the one of the plurality of second rings by an apex of the one of the plurality of second rings that is not connected to the adjacent one of the plurality of second rings.

19. The stent of claim 1, wherein attachment of the at least one connector to the ring strut is offset from the actual peak of the apex of the respective ring strut.

20. The stent of claim 13, wherein attachment of the substantially straight connector to the one of the plurality of second rings is offset from an actual peak of the apex of the one of the plurality of second rings.

21. The stent of claim 1, wherein the first stiffness is substantially constant along the length of the first stent segment and the second stiffness is substantially constant along the length of the second stent segment.

22. The stent of claim 1, wherein the first chronic outward force is substantially constant along the length of the first stent segment and the second chronic outward force is substantially constant along the length of the second stent segment.

23. The stent of claim 1, further comprising a third stent segment between the first stent segment and the second stent segment, the third stent segment comprising a plurality of third rings connected to one another to form a series of said third rings, the third stent segment having a third stiffness that varies along a length of the third stent segment from the first stent segment to the second stent segment.

24. The stent of claim 1, further comprising a third stent segment between the first stent segment and the second stent segment, the third stent segment comprising a plurality of third rings connected to one another to form a series of said third rings, the third stent segment having a third chronic outward force that varies along the length of the third stent segment from the first stent segment to the second stent segment.

25. The stent of claim 1, wherein the second segment is connected to the first segment via a smooth transition comprising a plurality of flexible connectors extending from adjacent at least one of the apices of the first stent segment to adjacent at least one apex of a third stent segment in a region adjacent the first stent segment and a plurality of flexible connectors extending from adjacent at least one of the apices of the second stent segment to adjacent at least one apex of the third stent segment in a region of the third stent adjacent the second stent segment.

26. The stent of claim 25, wherein adjacent at least one of the apices includes offset from an actual peak of the apex.

27. The stent of claim 25, wherein the smooth transition region comprises a plurality of flexible connectors extending from adjacent at least one of the apices of the first stent segment to adjacent at least one of the apices of the second stent segment.

28. The stent of claim 27, wherein adjacent at least one of the apices includes offset from an actual peak of the apex.

29. The stent of claim 1, wherein diameter of the first stent segment is substantially the same as the second stent segment in an expanded state.

30. The stent of claim 24, wherein the diameter of the first segment, the second stent segment and the third stent segment are substantially the same in an expanded state.

\* \* \* \* \*